(12) United States Patent
Danilevskaya et al.

(10) Patent No.: US 8,222,484 B2
(45) Date of Patent: Jul. 17, 2012

(54) FLORAL TRANSITION GENES IN MAIZE AND USES THEREOF

(75) Inventors: Olga Danilevskaya, Johnston, IA (US); Milo J Auckerman, Newark, DE (US); Pedro Hermon, Johnston, IA (US); Evgueni Ananiev, Johnston, IA (US); David Mark Shirbroun, West Des Moines, IA (US); Michael G Muszynski, Johnston, IA (US)

(73) Assignees: Pioneer Hi-Bred International, Inc., Johnston, IA (US); E.I. duPont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/888,469

(22) Filed: Sep. 23, 2010

(65) Prior Publication Data
US 2011/0010799 A1    Jan. 13, 2011

Related U.S. Application Data

(62) Division of application No. 11/614,120, filed on Dec. 21, 2006, now Pat. No. 7,842,851.

(51) Int. Cl.
*C12N 15/29* (2006.01)
*C12N 15/82* (2006.01)
*C12N 5/04* (2006.01)
*A01H 5/00* (2006.01)
*A01H 5/10* (2006.01)

(52) U.S. Cl. .................. 800/278; 536/24.1; 435/320.1; 435/419; 800/298; 800/320; 800/320.1; 800/290

(58) Field of Classification Search .............. None
See application file for complete search history.

(56) References Cited

U.S. PATENT DOCUMENTS

| | | | |
|---|---|---|---|
| 6,077,994 A | 6/2000 | Coupland et al. | |
| 6,140,085 A | 10/2000 | Dean et al. | |
| 6,310,271 B1 * | 10/2001 | Hanson et al. | 800/278 |
| 6,337,430 B1 * | 1/2002 | Ishige et al. | 800/278 |
| 6,573,430 B1 | 6/2003 | Bradley et al. | |

OTHER PUBLICATIONS

Benfey et al (1989, EMBO J, 8(8):2195-2202).*
Benfey et al (1990, Science 250:959-966).*
Benfey et al (1989, EMBO J, 8(8):2195-2202.*
Trevaskis, B., et al.; "MADS box genes control vernalization-induced flowering in cereals"; PNAS (Oct. 28, 2003) 100(22):13099-13104; National Academy of Sciences; United States.
Hartman, U., et al.; "Molecular cloning of SVP: a negative regulator of the floral transition in *Arabidopsis*"; The Plant Journal (2000) 21(4):351-360; Blackwell Science Ltd.; Oxford, England.
Masiero, S., et al.; "Incomposita: a MADS-box gene controlling prophyll development and floral meristem identity in *Antirrhinum*"; Development (2004) 131:5981-5990; The Company of Biologists; Cambridge, England.
Purugganan, M.D., et al.; "Molecular Evolution of Flower Development: Diversification of the Plant MADS-Box Regulatory Gene Family"; Genetics (May 1995) 140:245-356; The Genetics Society of America; Pittsburgh, PA, United States.
Saedler, H., et al.; "MADS-box genes are involved in floral development and evolution"; Acta Biochimica Polonica (2001) 48(2): 351-358; Institute of Experimental Biology; Poland.
Blazquez, M., et al.; "Flowering on time: genes that regulate the floral transition"; EMBO Reports (2001) 2(12):1078-1082; European Molecular Biology Organization; London, England.
Hong-Bo, S., et al.; "Plant Gene Regulatory Network System Under Abiotic Stress"; Acta Biologica Szegediensis (2006) 50(1-2):1-9; University of Szeged, Szeged, Hungary.

* cited by examiner

*Primary Examiner* — Stuart F. Baum
(74) *Attorney, Agent, or Firm* — Pioneer Hi-Bred Int'l Inc

(57) ABSTRACT

The invention provides isolated floral transition nucleic acids and their encoded proteins. The present invention provides methods and compositions relating to altering floral transition in plants. The invention further provides regulatory elements, recombinant expression cassettes, host cells, and transgenic plants.

13 Claims, 5 Drawing Sheets

FLORAL TRANSITION GENES IN MAIZE AND USES THEREOF

RELATED APPLICATIONS

This application is a division of U.S. patent application Ser. No. 11/614,120 filed Dec. 21, 2006, now U.S. Pat. No. 7,842,851 which claims the benefit of U.S. patent application Ser. No. 10/868,990, filed Jun. 16, 2004, now U.S. Pat. No. 7,279,615 which issued on Oct. 9, 2007 and of U.S. Patent Application Ser. No. 60/478,777, filed Jun. 16, 2003, all of which are incorporated herein by reference.

TECHNICAL FIELD

The present invention relates generally to plant molecular biology. More specifically, it relates to nucleic acids and methods for modulating their expression thereby controlling flowering time and flower/seed production in plants.

BACKGROUND OF THE INVENTION

Flowering in plants is a consequence of the transition of the shoot apical meristems from vegetative to reproductive growth in response to environmental and internal signals. Currently, there is little information about the regulation of flowering time in maize. Id1 gene (indeterminate 1) is the only maize cloned gene with a clear role in the floral transition (Colasanti, et al., (1998) *Cell* 93:593-603). The Id1 gene encodes a transcription factor and regulates the production of a transmissible signal in the immature leaves that induces the transition of the shoot apical meristems from vegetative to reproductive development.

Flowering time determines maturity and that is an important agronomic trait. Genes that control the transition from vegetative to reproductive growth are essential for manipulation of flowering time. Flowering genes will provide opportunities for enhanced crop yield, adaptation of germplasm to different climatic zones and synchronous flowering for hybrid seed production. Developing early-flowering inbred lines will facilitate the movement of elite germplasm across maturity zones. Flowering genes also provide an opportunity for engineering vernalized corn, enabling fall planting and over-wintering. Vernalization may be achieved by the over expression of the activator of flowering or the down-regulation of repressors of flowering in transgenic plants.

SUMMARY OF THE INVENTION

Generally, it is the object of the present invention to provide nucleic acids and proteins relating to floral transition. It is an object of the present invention to provide transgenic plants comprising the nucleic acids of the present invention and methods for modulating, in a transgenic plant, the expression of the nucleic acids of the present invention.

Therefore, in one aspect the present invention relates to an isolated nucleic acid comprising a member selected from the group consisting of (a) a polynucleotide having a specified sequence identity to a polynucleotide of the present invention; (b) a polynucleotide which is complementary to the polynucleotide of (a) and (c) a polynucleotide comprising a specified number of contiguous nucleotides from a polynucleotide of (a) or (b). The isolated nucleic acid can be DNA.

In other aspects the present invention relates to: 1) recombinant expression cassettes, comprising a nucleic acid of the present invention operably linked to a promoter, 2) a host cell into which has been introduced the recombinant expression cassette and 3) a transgenic plant comprising the recombinant expression cassette. The host cell or plant is optionally a maize cell or maize plant, respectively.

The present invention provides compositions and methods for modulating flowering time in plants. Overexpression of he disclosed sequences leads to early flowering and inhibition causes late flowering and indeterminate ear initiation. Methods for expressing these sequences in a plant for modifying maturity and flowering time in plants are provided as well as expression constructs, vectors, transformed cells and plants. The sequences disclosed include regulatory elements and promoter sequences that are natively associated with the polynucleotides disclosed herein, thereby providing the meristem specific promoters that can be used to control plant growth, development, herbicide and insect resistance. The over-expression of genes that are activators or repressors of flowering in transgenics under direction of tissue and/or gene specific promoters allows one to control the timing of flower formation without ectopic expression of unwanted proteins in other tissues. Controlled manipulation of flowering time will provide opportunities for enhancing crop yield, adaptation of germplasm to different climatic zones and synchronous flowering for hybrid seed production.

DETAILED DESCRIPTION OF THE INVENTION

Overview

Figure 1:
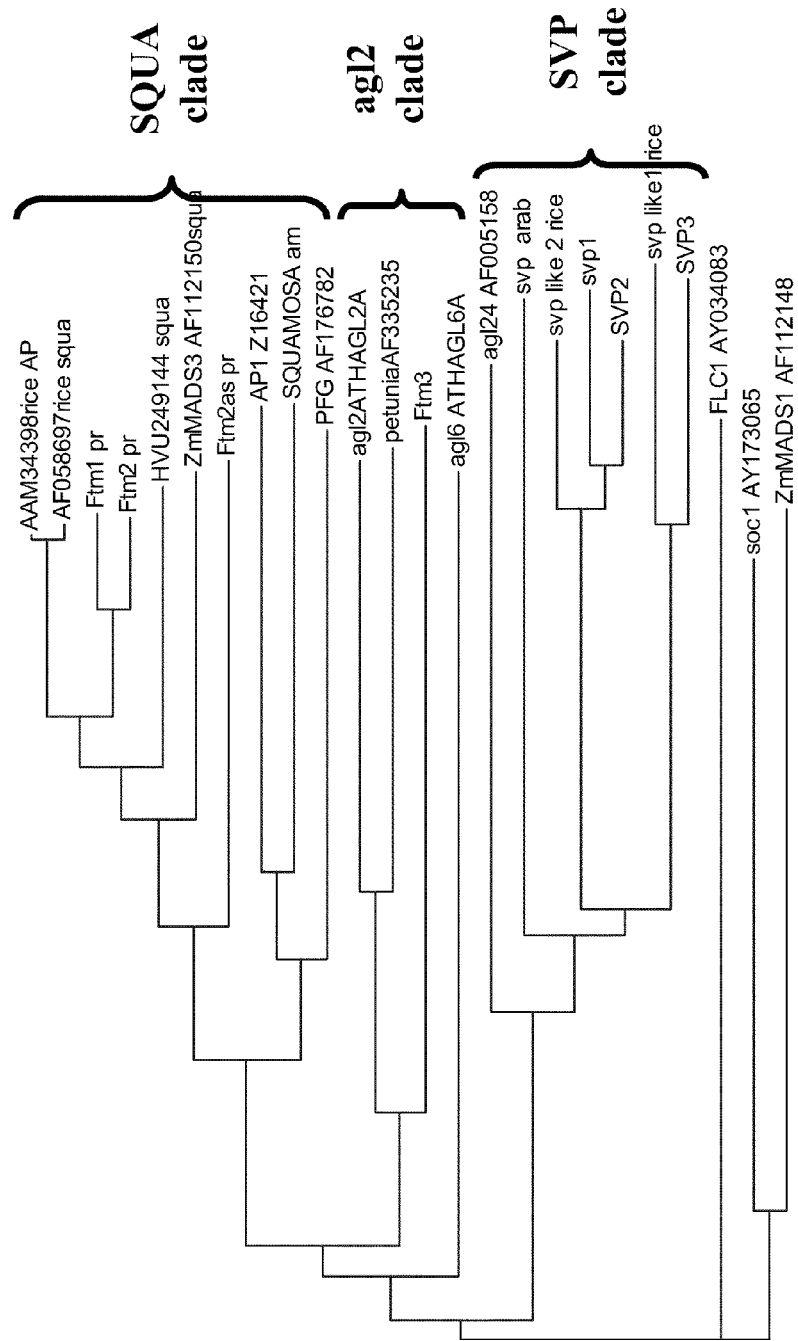
FIG. 1 provides a phylogenetic analysis of novel MADS box genes SVP and FTM and delimits them into three separate clades, SQUAMOSA-like (FTM1,2), AGL2-like (FTM3) and SVP-like (SVP1,2,3).

A set of new maize MADS box genes regulating flowering time were discovered in the shoot apical meristems using the massively parallel signature sequencing (MPSS) technology from Lynx Therapeutics (Haywood, Calif.). Six MADS box genes were identified that show changes in transcriptional activity during the floral transition. Genes named FTM1, FTM2 and FTM3 (stands for Floral Transition MADS) are up-regulated during floral transition consistent with their functions as activators of flowering. Genes named SVP1, SVP2 and SVP3 by homology to the *Arabidopsis* gene SVP (stands for Short Vegetative Phase, Hartmann, et al., (2000) *Plant Journal* 21:351-360) are down-regulated during the floral transition consistent with their function as repressors of flowering.

MADS-box genes belong to a large family of regulatory genes that possess a characteristic DNA binding domain, MADS-box. Members of this gene family display primarily floral-specific expression and play important roles in plant development. Phlyogenetic analyses demonstrate that members of the plant MADS-box gene family are organized into a dozen distinct gene groups which reflect the true phylogeny of the MADS box gene families and their functional similarity (Theissen, et al., (1996) *J Mol Evol.* 43:484-516). Phylogenetic analysis of discovered MADS box genes, SVP and FTM delimits them into separate clades, STMADS11 (SVP) SQUAMOSA-like (FTM1,2) and AGL2 (FTM3). STMADS11 family includes tomato STMADS genes and the *Arabidopsis* SVP (Hartmann, et al., (2000) *Plant Journal* 21:351-360). Those genes are known to be negative regulators of the floral transition. SQUAMOSA-like family determines the identity of the floral meristem (Klein, et al., (1996) *Mol Gen Genet.* 250:7-16). Because the shared evolutionary history appears to reflect the distinct functional roles of MADS families in flower development, we proposed that discovered maize SVP genes are negative regulators of flowering and FTM genes are activators of the floral development.

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues and/or in quantities, which are uncharacteristic of non-recombinantly engineered plants. Thus, the present invention provides utility in such exemplary applications as providing a means to control expression of genes involved in enhancing crop yield, adaptation of germplasm to different climatic zones and synchronous flowering for hybrid seed production. For example, in plants of interest, manipulation of the floral transitional genes of the present invention could affect the expression of the activator of flowering or the down-regulation of repressors of flowering. The over-expression of activators in transgenics or inhibition of repressors by chemical treatment, co-suppression, RNAi, antisense RNA or mutations may lead to early flowering phenotypes which may find utilities in crops such as corn, soybean, rice and wheat due to effects on yield, seed production and germplasm adaptation to a wide range of environmental conditions. Conversely, the over-expression of repressors or inhibition of activators by chemical treatment, co-suppression, RNAi, antisense RNA or mutations, may suppress flower formation, which is useful for crops such as spinach or lettuce where leaves are desired and seed formation is not. The use of conditional promoters to control activators and repressors allows one to control the timing of flower formation, to delay flowering when vegetative growth is advantageous or accelerate flowering in breeding where reduced generation time is desired.

The present invention provides useful alleles for breeding programs through association mapping of flowering phenotypes with specific haplotypes of flowering genes. Nucleotide sequencing polymorphisms defining specific haplotypes (alleles, orthologues, derivatives) may be converted into molecular markers and used during the breeding programs for selection of "early" and "late" inbred lines in marker assisted selection.

The present invention also provides isolated nucleic acids comprising polynucleotides of sufficient length and complementarity to a gene of the present invention to use as probes or amplification primers in the detection, quantitation or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs or paralogs of the gene or for site directed mutagenesis in eukaryotic cells (see, e.g., U.S. Pat. No. 5,565,350). The isolated nucleic acids of the present invention can also be used for recombinant expression of their encoded polypeptides or for use as immunogens in the preparation and/or screening of antibodies. The isolated nucleic acids of the present invention can also be employed for use in sense or antisense suppression of one or more genes of the present invention in a host cell, tissue or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme or enzymes). The present invention also provides proteins comprising at least one epitope from a polypeptide of the present invention. The proteins of the present invention can be employed in assays for enzyme agonists or antagonists of enzyme function or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species or for purification of polypeptides of the present invention.

The isolated nucleic acids and polypeptides of the present invention can be used over a broad range of plant types, particularly monocots such as the species of the family Gramineae including *Hordeum, Secale, Triticum, Sorghum* (e.g., *S. bicolor*) and *Zea* (e.g., *Z. mays*). The isolated nucleic acid and proteins of the present invention can also be used in species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browallia, Glycine, Pisum, Phaseolus, Lolium, Oryza,* and *Avena.*

Definitions

Units, prefixes and symbols may be denoted in their SI accepted form. Unless otherwise indicated, nucleic acids are written left to right in 5' to 3' orientation; amino acid sequences are written left to right in amino to carboxyl orientation, respectively. Numeric ranges recited within the specification are inclusive of the numbers defining the range and include each integer within the defined range. Amino acids may be referred to herein by either commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical and electronics terms as used herein are as defined in The New IEEE Standard Dictionary of Electrical and Electronics Terms (5$^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS) and strand displacement amplification (SDA). See, e.g., *Diagnostic Molecular Microbiology: Principles and Applications,* Persing, et al., Ed., American Society for Microbiology, Washington, D.C. (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal and fungal mitochondria, the bacterium *Mycoplasma capricolumn* or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray, et al., (1989) *Nucl. Acids Res.* 17:477-498). Thus, the maize preferred codon for a particular amino acid may be derived from known gene sequences from maize. Maize codon usage for 28 genes from maize plants is listed in Table 4 of Murray, et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual,* Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

The term "gene activity" refers to one or more steps involved in gene expression, including transcription, translation and the functioning of the protein encoded by the gene.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli* or eukaryotic cells such as yeast, insect, amphibian or mammalian cells. Preferably, host cells are monocotyledonous or dicotyledonous plant cells. A particularly preferred monocotyledonous host cell is a maize host cell.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

The term "isolated" refers to material, such as a nucleic acid or a protein, which is: (1) substantially or essentially free from components which normally accompany or interact with it as found in its natural environment. The isolated material optionally comprises material not found with the material in its natural environment or (2) if the material is in its natural environment, the material has been synthetically altered or synthetically produced by deliberate human intervention and/ or placed at a different location within the cell. The synthetic alteration or creation of the material can be performed on the material within or apart from its natural state. For example, a naturally-occurring nucleic acid becomes an isolated nucleic acid if it is altered or produced by non-natural, synthetic methods or if it is transcribed from DNA which has been altered or produced by non-natural, synthetic methods. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling, et al., PCT/US93/03868. The isolated nucleic acid may also be produced by the synthetic re-arrangement ("shuffling") of a part or parts of one or more allelic forms of the gene of interest. Likewise, a naturally-occurring nucleic acid (e.g., a promoter) becomes isolated if it is introduced to a different locus of the genome. Nucleic acids which are "isolated," as defined herein, are also referred to as "heterologous" nucleic acids.

Unless otherwise stated, the term "floral transition nucleic acid" is a nucleic acid of the present invention and means a nucleic acid comprising a polynucleotide of the present invention (a "floral transition polynucleotide") encoding a floral transition polypeptide. A "floral transition gene" is a gene of the present invention and refers to a full-length floral transition polynucleotide.

As used herein, "nucleic acid" includes reference to a deoxyribonucleotide or ribonucleotide polymer or chimeras thereof, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism or of a tissue from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook, et al., *Molecular Cloning—A Laboratory Manual,* 2nd ed., Vol. 1-3 (1989) and *Current Protocols in Molecular Biology,* Ausubel, et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide or chimeras or analogs thereof that have the essential nature of a natural deoxy- or ribo-nucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically-, enzymatically- or metabolically-modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally-occurring amino acid, as well as to naturally-occurring amino acid polymers. The essential nature of such analogues of naturally-occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific and inducible promoters represent the class of "non-constitutive" promoters. A "constitutive" promoter is a promoter which is active in most tissues under most environmental conditions.

The term "floral transitional polypeptide" is a polypeptide of the present invention and refers to one or more amino acid sequences, in glycosylated or non-glycosylated form. The term is also inclusive of fragments, variants, homologs, alleles or precursors (e.g., preproproteins or proproteins) thereof. A "floral transitional protein" is a protein of the present invention and comprises a floral transitional polypeptide.

As used herein "recombinant" includes reference to a cell or vector that has been modified by the introduction of a heterologous nucleic acid or to a cell derived from a cell so modified. Thus, for example, recombinant cells express genes that are not found in identical form within the native (non-recombinant) form of the cell or exhibit altered expression of native genes, as a result of deliberate human intervention. The term "recombinant" as used herein does not encompass the alteration of the cell or vector by events (e.g., spontaneous mutation, natural transformation, transduction or transposition) occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

The term "residue" or "amino acid residue" or "amino acid" are used interchangeably herein to refer to an amino acid that is incorporated into a protein, polypeptide or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity and most preferably 100% sequence identity (i.e., complementary) with each other.

The term "stringent conditions" or "stringent hybridization conditions" includes reference to conditions under which a probe will selectively hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993) and *Current Protocols in Molecular Biology*, Chapter 2, Ausubel, et al., Eds., Greene Publishing and Wiley-Interscience, New York (1995). Hybridization and/or wash conditions can be applied for at least 10, 30, 60, 90, 120 or 240 minutes.

As used herein, "transcription factor" includes reference to a protein which interacts with a DNA regulatory element to affect expression of a structural gene or expression of a second regulatory gene. "Transcription factor" may also refer to the DNA encoding said transcription factor protein. The function of a transcription factor may include activation or repression of transcription initiation.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in introduction of a polynucleotide of the present invention into a host cell. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a) "reference sequence", (b) "comparison window", (c) "sequence identity" and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100 or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, (1981) *Adv. Appl. Math.* 2:482; by the homology alignment algorithm of Needleman and Wunsch, (1970) *J. Mol. Biol.* 48:443; by the search for similarity method of Pearson and Lipman, (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA and TFASTA in the Wisconsin Genetics Software Package®, GCG® programs (Accelrys, Inc., San Diego, Calif.); the CLUSTAL program is well described by Higgins and Sharp, (1988) *Gene* 73:237-244; Higgins and Sharp, (1989) CABIOS 5:151-153; Corpet, et al., (1988) *Nucleic Acids Research* 16:10881-90; Huang, et al., (1992) *Computer Applications in the Biosciences* 8:155-65 and Pearson, et al., (1994) *Methods in Molecular Biology* 24:307-331.

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments or the end of either sequence is reached. The BLAST algorithm parameters W, T and X determine the sensitivity and speed of the alignment. The BLASTN program (for nucleotide sequences) uses as defaults a wordlength (W) of 11, an expectation (E) of 10, a cutoff of 100, M=5, N=−4 and a comparison of both strands. For amino acid sequences, the BLASTP program uses as defaults a wordlength (W) of 3, an expectation (E) of 10 and the BLOSUM62 scoring matrix (see, Henikoff and Henikoff, (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul, *Proc. Nat'l. Acad. Sci. USA* 90:5873-5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.*, 17:149-163) and XNU (Claverie and States, (1993) *Comput. Chem.*, 17:191-201) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch ((1970) *J. Mol. Biol.* 48:443-453) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package® for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, Henikoff and Henikoff, (1989) *Proc. Natl. Acad. Sci. USA* 89:10915).

Multiple alignment of the sequences can be performed using the CLUSTAL method of alignment (Higgins and Sharp, (1989) *CABIOS.* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.,* 4:11-17 e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:

(a) a polynucleotide encoding a polypeptide of SEQ ID NOS: 2, 4, 6, 8, 10, 12 or 14 including the exemplary polynucleotide of SEQ ID NOS: 1, 3, 5, 7, 9, 11 or 13;

(b) a polynucleotide which is the product of amplification from a *Zea mays* nucleic acid library using primer pairs which selectively hybridize under stringent conditions to loci within a polynucleotide selected from SEQ ID NOS: 1, 3, 5, 7, 9, 11 or 13;

(c) a polynucleotide which selectively hybridizes to a polynucleotide of (a) or (b);

(d) a polynucleotide having a specified sequence identity with polynucleotides of (a), (b) or (c);

(e) a polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) sequences complementary to polynucleotides of (a), (b), (d) or (e); and (h) a polynucleotide comprising at least 50 contiguous nucleotides from a polynucleotide of (a), (b), (c), (d), (e) or (f).

A. Polynucleotides Encoding a Polypeptide of the Present Invention

As indicated in (a), above, the present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Thus, each silent variation of a nucleic acid which encodes a polypeptide of the present invention is implicit in each described polypeptide sequence and is within the scope of the present invention. Accordingly, the present invention includes the polynucleotide of SEQ ID NOS: 1, 3, 5, 7, 9, 11 or 13 and polynucleotides encoding a polypeptide of SEQ ID NO: 2, 4, 6, 8, 10, 12 or 14.

B. Polynucleotides Amplified from a *Zea mays* Nucleic Acid Library

As indicated in (b), above, the present invention provides an isolated nucleic acid comprising a polynucleotide of the present invention, wherein the polynucleotides are amplified from a *Zea mays* nucleic acid library. *Zea mays* lines B73, PHRE1, A632, BMS-P2#10, W23 and Mo17 are known and publicly available. Other publicly known and available maize lines can be obtained from the Maize Genetics Cooperation (Urbana, Ill.). The nucleic acid library may be a cDNA library, a genomic library or a library generally constructed from nuclear transcripts at any stage of intron processing. cDNA libraries can be normalized to increase the representation of relatively rare cDNAs. In optional embodiments, the cDNA library is constructed using a full-length cDNA synthesis method. Examples of such methods include Oligo-Capping (Maruyama and Sugano, (1994) *Gene* 138:171-174), Biotinylated CAP Trapper (Carninci, et al., (1996) *Genomics* 37:327-336) and CAP Retention Procedure (Edery, et al. (1995) *Molecular and Cellular Biology* 15:3363-3371). cDNA synthesis is often catalyzed at 50-55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and RetroAmp Reverse Transcriptase (Epicentre). Rapidly-growing tissues or rapidly-dividing cells are preferably used as mRNA sources, particularly lateral root initiation regions of adventitious roots in soil-grown maize plants.

The present invention also provides subsequences of the polynucleotides of the present invention. A variety of subsequences can be obtained using primers which selectively hybridize under stringent conditions to at least two sites within a polynucleotide of the present invention or to two sites within the nucleic acid which flank and comprise a polynucleotide of the present invention or to a site within a polynucleotide of the present invention and a site within the nucleic acid which comprises it. Primers are chosen to selectively hybridize, under stringent hybridization conditions, to a polynucleotide of the present invention. Generally, the primers are complementary to a subsequence of the target nucleic acid which they amplify but may have a sequence identity ranging from about 85% to 99% relative to the polynucleotide sequence which they are designed to anneal to. As those skilled in the art will appreciate, the sites to which the primer pairs will selectively hybridize are chosen such that a single contiguous nucleic acid can be formed under the desired amplification conditions.

In optional embodiments, the primers will be constructed so that they selectively hybridize under stringent conditions to a sequence (or its complement) within the target nucleic acid, which comprises the codon encoding the carboxy or amino terminal amino acid residue (i.e., the 3' terminal coding region and 5' terminal coding region, respectively) of the polynucleotides of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Thus, the primers can be at least 15, 18, 20, 25, 30, 40 or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity) or verifying the presence of one or more epitopes, which are specific to a polypeptide of the present invention. Methods for protein synthesis from PCR derived templates are known in the art and available commercially. See, e.g., Amersham Life Sciences, Inc, Catalog '97, p. 354.

Methods for obtaining 5' and/or 3' ends of a vector insert are well known in the art. See, e.g., RACE (Rapid Amplification of Complementary Ends) as described in Frohman, in PCR Protocols: A Guide to Methods and Applications, Innis, et al., Eds. (Academic Press, Inc., San Diego), pp. 28-38 (1990)); see also, U.S. Pat. No. 5,470,722 and *Current Protocols in Molecular Biology*, Unit 15.6, Ausubel, et al., Eds., Greene Publishing and Wiley-Interscience, New York (1995); Frohman and Martin, (1989) *Techniques* 1:165.

C. Polynucleotides which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: maize, canola, soybean, cotton, wheat, sorghum, sunflower, alfalfa, oats, sugar cane, millet, barley and rice. Optionally, the cDNA library comprises at least 30% to 95% full-length sequences (for example, at least 30%, 40%, 50%, 60%, 70%, 80%, 90% or 95% full-length sequences). The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% to 80% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed in sections (A), (B) or (C), above. Identity can be calculated using, for example, the BLAST, CLUSTALW, or GAP algorithms under default conditions. The percentage of identity to a reference sequence is at least 57% and, rounded upwards to the nearest integer, can be expressed as an integer selected from the group of integers consisting of from 57 to 99. Thus, for example, the percentage of identity to a reference sequence can be at least 60%, 75%, 80%, 85%, 90% or 95%.

Optionally, the polynucleotides of this embodiment will encode a polypeptide that will share an epitope with a polypeptide encoded by the polynucleotides of sections (A), (B) or (C). Thus, these polynucleotides encode a first polypeptide which elicits production of antisera comprising antibodies which are specifically reactive to a second polypeptide encoded by a polynucleotide of (A), (B) or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B) or (C) or for purification of, or in immunoassays for, polypeptides encoded by the polynucleotides of (A), (B) or (C). The polynucleotides of this embodiment embrace nucleic acid sequences, which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Numbers WO 91/17271, WO 91/18980, WO 91/19818 and WO 93/08278. Other systems for generating libraries of peptides have aspects of both in vitro chemical synthesis and recombinant methods. See, PCT Patent Publication Numbers WO 92/05258, WO 92/14843 and WO 97/20078. See also, U.S. Pat. Nos. 5,658,754 and 5,643,768. Peptide display libraries, vectors and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45 or 50, contiguous amino acids from the prototype polypeptide. Further, the number of such subsequences encoded by a polynucleotide of the instant embodiment can be any integer selected from the group consisting of from 1 to 20, such as 2, 3, 4 or 5. The subsequences can be separated by any integer of nucleotides from 1 to the number of nucleotides in the sequence such as at least 5, 10, 15, 25, 50, 100 or 200 nucleotides.

The proteins encoded by polynucleotides of this embodiment, when presented as an immunogen, elicit the production of polyclonal antibodies, which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera, which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full-length polypeptide of the present invention, more preferably within 10% or 5% and most preferably within 3%, 2% or 1% of a full-length polypeptide of the present invention.

Optionally, the polynucleotides of this embodiment will encode a protein having a specific enzymatic activity at least 50%, 60%, 80% or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50% and most preferably at least 60%, 70%, 80%, 90% or 95% the $k_{cat}/K_m$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow or rapid quenching techniques), flash photolysis or relaxation methods (e.g., temperature jumps) in conjunction with such exemplary methods of measuring as spectrophotometry, spectrofluorimetry, nuclear magnetic resonance or radioactive procedures. Kinetic values are conveniently obtained using a Lineweaver-Burk or Eadie-Hofstee plot.

F. Polynucleotides Complementary to the Polynucleotides of (A)-(E)

As indicated in (f), above, the present invention provides isolated nucleic acids comprising polynucleotides complementary to the polynucleotides of paragraphs (A), (B), (D) or (E), above. As those of skill in the art will recognize, complementary sequences base-pair throughout the entirety of their length with the polynucleotides of sections (A), (B), (D) or (E) (i.e., have 100% sequence identity over their entire length). Complementary bases associate through hydrogen bonding in double-stranded nucleic acids. For example, the following base pairs are complementary: guanine and cytosine; adenine and thymine and adenine and uracil.

G. Polynucleotides which are Subsequences of the Polynucleotides of (A)-(F)

As indicated in (h), above, the present invention provides isolated nucleic acids comprising polynucleotides which comprise at least 50 contiguous bases from the polynucleotides of sections (A) through (G) as discussed above. The length of the polynucleotide is given as an integer selected from the group consisting of from at least 50 to the length of the nucleic acid sequence of which the polynucleotide is a subsequence. Thus, for example, polynucleotides of the present invention are inclusive of polynucleotides comprising at least 50, 60, 75 or 100 contiguous nucleotides in length from the polynucleotides of (A)-(G). Optionally, the number of such subsequences encoded by a polynucleotide of the instant embodiment can be any integer selected from the group consisting of from 1 to 20, such as 2, 3, 4 or 5. The subsequences can be separated by any integer of nucleotides from 1 to the number of nucleotides in the sequence such as at least 5, 10, 15, 25, 50, 100 or 200 nucleotides.

A subsequence of the present invention can comprise structural characteristics of the sequence from which it is derived. Alternatively, a subsequence can lack certain structural characteristics of the larger sequence from which it is derived, such as a poly (A) tail. Optionally, a subsequence from a polynucleotide encoding a polypeptide having at least one epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it is derived. Subsequences can be used to modulate or detect gene expression by introducing into the subsequences compounds, which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques or combinations thereof. In some embodiments, the polynucleotides of the present invention will be cloned, amplified, or otherwise constructed from a monocot. In preferred embodiments the monocot is Zea mays.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb and frequently less than 10 kb. Use of cloning vectors, expression vectors, adapters and linkers is well known and extensively described in the art. For a description of various nucleic acids see, for example, Stratagene Cloning Systems, Catalogs 1995, 1996, 1997 (La Jolla, Calif.) and Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. Isolation of RNA, and construction of cDNA and genomic libraries is well known to those of ordinary skill in the art. See, e.g., *Plant Molecular Biology: A Laboratory Manual*, Clark, Ed., Springer-Verlag, Berlin (1997) and *Current Protocols in Molecular Biology*, Ausubel, et al., Eds., Greene Publishing and Wiley-Interscience, New York (1995).

A number of cDNA synthesis protocols have been described which provide substantially pure full-length cDNA libraries. Substantially pure full-length cDNA libraries are constructed to comprise at least 90% and more preferably at least 93% or 95% full-length inserts amongst clones containing inserts. The length of insert in such libraries can be from 0 to 8, 9, 10, 11, 12, 13 or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci, et al., (1996) *Genomics,* 37:327-336. Other methods for producing full-length libraries are known in the art. See, e.g., Edery, et al., (1995) *Mol. Cell Biol.* 15(6):3363-3371; and PCT Application WO 96/34981.

A1. Normalized or Subtracted cDNA Libraries

A non-normalized cDNA library represents the mRNA population of the tissue from which it was made. Since unique clones are out-numbered by clones derived from highly expressed genes, their isolation can be laborious. Normalization of a cDNA library is the process of creating a library in which each clone is more equally represented. Construction of normalized libraries is described in Ko, (1990) *Nucl. Acids. Res.,* 18(19):5705-5711; Patanjali, et al., (1991) *Proc. Natl. Acad. U.S.A.,* 88:1943-1947; U.S. Pat. Nos. 5,482,685 and 5,637,685. In an exemplary method described by Soares, et al., (1994) *Proc. Natl. Acad. Sci. USA,* 91:9228-9232.

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote, et al., (1997) *Plant Molecular Biology: A Laboratory Manual*, Clark, Ed., Springer-Verlag, Berlin; Kho and Zarbl, (1991) *Technique,* 3(2):58-63; Sive and St. John, (1988) *Nucl. Acids Res.,* 16(22):10937; *Current Protocols in Molecular Biology*, Ausubel, et al., Eds., Greene Publishing and Wiley-Interscience, New York (1995) and Swaroop et al., (1991) *Nucl. Acids Res.,* 19(8):1954. cDNA subtraction kits are commercially available. See, e.g., PCR-Select (Clontech, Palo Alto, Calif.).

To construct genomic libraries, large segments of genomic DNA are generated by fragmentation, e.g., using restriction endonucleases and are ligated with vector DNA to form concatemers that can be packaged into the appropriate vector. Methodologies to accomplish these ends and sequencing methods to verify the sequence of nucleic acids are well known in the art. Examples of appropriate molecular biological techniques and instructions sufficient to direct persons of skill through many construction, cloning and screening methodologies are found in Sambrook, et al., *Molecular Cloning: A Laboratory Manual,* 2nd Ed., Cold Spring Harbor Laboratory, Vols. 1-3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing or for other purposes. The T4 gene 32 protein (Boehringer Mannheim) can be used to improve yield of long PCR products.

PCR-based screening methods have been described. Wilfinger, et al., describe a PCR-based method in which the longest cDNA is identified in the first step so that incomplete clones can be eliminated from study. *BioTechniques,* 22(3): 481-486 (1997). Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-99; the phosphodiester method of Brown, et al., (1979) *Meth. Enzymol.* 68:109-151; the diethylphosphoramidite method of Beaucage, et al., (1981) *Tetra. Lett.* 22:1859-1862; the solid phase phosphoramidite triester method described by Beaucage and Caruthers, (1981) *Tetra. Letts.* 22(20):1859-1862, e.g., using an automated synthesizer, e.g., as described in Needham-VanDevanter, et al., (1984) *Nucleic Acids Res.,* 12:6159-6168 and the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full-length polypeptide of the present invention, can be used to construct a recombinant expression cassette, which can be introduced into the desired host cell. A recombinant expression cassette will typically comprise a polynucleotide of the present invention operably linked to transcriptional initiation regulatory sequences, which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated or cell- or tissue-specific/selective expression), a transcription initiation start site, a ribosome binding site, an RNA processing signal, a transcription termination site and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions or the presence of light. Examples of inducible promoters are the Adh1 promoter, which is inducible by hypoxia or cold stress, the Hsp70 promoter, which is inducible by heat stress and the PPDK promoter, which is inducible by light.

Examples of promoters under developmental control include promoters that initiate transcription only or preferentially, in certain tissues, such as leaves, roots, fruit, seeds or flowers. Exemplary promoters include the root cdc2a promoter (Doerner, et al., (1996) *Nature* 380:520-523), the root peroxidase promoter from wheat (Hertig, et al., (1991) *Plant Mol. Biol.* 16:171-174) or flower specific promoters (Maizel, et al., (2004) *Plant J*. Apr; 38(1):164-171). The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase or alter concentration and/or composition of the proteins of the present invention in a desired tissue. Thus, in some embodiments, the nucleic acid construct will comprise a promoter functional in a plant cell, such as in Zea mays, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up- or down-regulate expression of a polynucleotide of the present invention. For example, endogenous promoters can be altered in vivo by mutation, deletion, and/or substitution (see, Kmiec, U.S. Pat. No. 5,565,350; Zarling, et al., PCT/US93/03868) or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions and methods for making, heterologous promoters and/or enhancers operably linked to a native, endogenous (i.e., non-heterologous) form of a polynucleotide of the present invention.

If polypeptide expression is desired, it is generally desirable to include a polyadenylation region at the 3'-end of a polynucleotide coding region. The polyadenylation region can be derived from the natural gene, from a variety of other plant genes or from T-DNA. The 3' end sequence to be added can be derived from, for example, the nopaline synthase or octopine synthase genes or alternatively from another plant gene or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, (1988) Mol. Cell Biol. 8:4395-4405; Callis et al., Genes Dev. 1: 1183-1200 (1987). Such intron enhancement of gene expression is typically greatest when placed near the 5' end of the transcription unit. Use of maize introns Adh1-S intron 1, 2, and 6, the Bronze-1 intron are known in the art. See generally, The Maize Handbook, Chapter 116, Freeling and Walbot, Eds., Springer, N.Y. (1994). The vector comprising the sequences from a polynucleotide of the present invention will typically comprise a marker gene which confers a selectable phenotype on plant cells. Typical vectors useful for expression of genes in higher plants are well known in the art and include vectors derived from the tumor-inducing (Ti) plasmid of Agrobacterium tumefaciens described by Rogers, et al., (1987) Meth. in Enzymol. 153:253-277.

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy, et al., (1988) Proc. Nat'l. Acad. Sci. (USA) 85:8805-8809 and Hiatt, et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., (1990) The Plant Cell 2:279-289 and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff, et al., (1988) Nature 334:585-591.

A variety of cross-linking agents, alkylating agents and radical generating species as pendant groups on polynucleotides of the present invention can be used to bind, label, detect and/or cleave nucleic acids. For example, Vlassov, et al., (1986) Nucleic Acids Res 14:4065-4076, describe covalent bonding of a single-stranded DNA fragment with alkylating derivatives of nucleotides complementary to target sequences. A report of similar work by the same group is that by Knorre, et al., (1985) Biochimie 67:785-789. Iverson and Dervan also showed sequence-specific cleavage of single-stranded DNA mediated by incorporation of a modified nucleotide which was capable of activating cleavage (J Am Chem Soc (1987) 109:1241-1243). Meyer, et al., (1989) J Am Chem Soc 111:8517-8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, et al., (1988) Biochemistry 27:3197-3203. Use of crosslinking in triple-helix forming probes was also disclosed by Home, et al., (1990) J Am Chem Soc 112:2435-2437. Use of N4, N4-ethanocytosine as an alkylating agent to crosslink to single-stranded oligonucleotides has also been described by Webb and Matteucci, (1986) J Am Chem Soc 108:2764-2765; Nucleic Acids Res (1986) 14:7661-7674; Feteritz, et al., (1991) J. Am. Chem. Soc. 113:4000. Various compounds to bind, detect, label and/or cleave nucleic acids are known in the art. See, for example, U.S. Pat. Nos. 5,543,507; 5,672,593; 5,484,908; 5,256,648 and, 5,681,941.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232, 529); balanced amino acids (e.g., hordothionins (U.S. Pat. Nos. 5,990,389; 5,885,801; 5,885,802 and 5,703,409); barley high lysine (Williamson, et al., (1987) *Eur. J. Biochem.* 165: 99-106 and WO 98/20122) and high methionine proteins (Pedersen, et al., (1986) *J. Biol. Chem.* 261:6279; Kirihara, et al., (1988) *Gene* 71:359 and Musumura, et al., (1989) *Plant Mol. Biol.* 12: 123)); increased digestibility (e.g., modified storage proteins (U.S. application Ser. No. 10/053,410, filed Nov. 7, 2001) and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792, 931); avirulence and disease resistance genes (Jones, et al., (1994) *Science* 266:789; Martin, et al., (1993) *Science* 262: 1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene) and glyphosate resistance (EPSPS gene)) and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see, U.S. Pat. No. 5,583,210), stalk strength, flowering time, drought or other abiotic stress resistance or transformation technology traits such as cell cycle regulation or gene targeting (e.g., WO 99/61619; WO 00/17364; WO 99/25821), the disclosures of which are herein incorporated by reference.

These stacked combinations can be created by any method, including but not limited to cross breeding plants by any conventional or TopCross methodology or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences of interest can be driven by the same promoter or by different promoters. In certain cases, it may be desirable to introduce a transformation cassette that will suppress the expression of a polynucleotide of interest. This may be accompanied by any combination of other suppression cassettes or overexpression cassettes to generate the desired combination of traits in the plant.

The random insertion of introduced DNA into the genome of host cells can be lethal if the foreign DNA happens to insert into, and thus mutate, a critically important native gene. In addition, even if a random insertion event does not impair the functioning of a host cell gene, the expression of an inserted foreign gene may be influenced by "position effects" caused by the surrounding genomic DNA. In some cases, the gene is inserted into sites where the position effects are strong enough to prevent the synthesis of an effective amount of product from the introduced gene.

Integration of polynucleotides of interest at a target site is possible using site-specific recombination systems (see, for example, WO 99/25821, herein incorporated by reference).

Another variation to minimize expression from random integration includes providing a promoter or transcription initiation region operably linked with the target site in an organism. The promoter will be 5' to the first recombination site. By transforming the organism with a transfer cassette comprising a coding region flanked by recombination sites corresponding to the sites in the target site and providing recombinase activity, functional linkage and expression of the coding region will occur upon integration of the transfer cassette into the target site by site-specific recombination. Alternatively, the target site may comprise a promoter and a translation start codon (ATG) operably linked 5' to the first recombination site. A transfer cassette comprising an ATG-less coding region is used. This arrangement further minimizes expression due to random integration of the transfer cassette, since expression would require the random integration to occur behind and endogenous promoter, and in the correct reading frame. (See, for example, WO 99/25821, herein incorporated by reference).

Proteins

The isolated proteins of the present invention comprise a polypeptide having at least 10 amino acids encoded by any one of the polynucleotides of the present invention as discussed more fully, above or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35 or 40 amino acids in length, often at least 50, 60, 70, 80 or 90 amino acids in length. Further, the number of such subsequences can be any integer selected from the group consisting of from 1 to 20, such as 2, 3, 4 or 5.

The present invention further provides a protein comprising a polypeptide having a specified sequence identity with a polypeptide of the present invention. The percentage of sequence identity is an integer selected from the group consisting of from 50 to 99. Exemplary sequence identity values include 60%, 65%, 70%, 75%, 80%, 85%, 90% and 95%. Sequence identity can be determined using, for example, the BESTFIT, GAP, CLUSTALW or BLAST algorithms.

As those of skill will appreciate, the present invention includes catalytically active polypeptides of the present invention (i.e., enzymes). Catalytically active polypeptides have a specific activity of at least 20%, 30% or 40% and preferably at least 50%, 60% or 70% and most preferably at least 80%, 90% or 95% that of the native (non-synthetic), endogenous polypeptide. Further, the substrate specificity ($k_{cat}/K_m$) is optionally substantially similar to the native (non-synthetic), endogenous polypeptide. Typically, the $k_{cat}/K_m$ will be at least 30%, 40% or 50%, that of the native (non-synthetic), endogenous polypeptide and more preferably at least 60%, 70%, 80% or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, supra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian or preferably plant cells. The cells produce the protein in a non-natural condition (e.g., in quantity, composition, location and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation and a transcription/translation terminator. One of skill would recognize that modifications can be made to a protein of the present invention without diminishing its biological activity. Some modifications may be made to facilitate the cloning, expression or incorporation of the targeting molecule into a fusion protein. Such modifications are well known to those of skill in the art and include, for example, a methionine added at the amino terminus to provide an initiation site or additional amino acids (e.g., poly His) placed on either terminus to create conveniently located purification sequences. Restriction sites or termination codons can also be introduced.

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for effective transformation/transfection may be employed.

A. Plant Transformation

A DNA sequence coding for the desired polypeptide of the present invention, for example a cDNA or a genomic sequence encoding a full-length protein, will be used to construct a recombinant expression cassette which can be introduced into the desired plant.

Isolated nucleic acid acids of the present invention can be introduced into plants according to techniques known in the art. Generally, recombinant expression cassettes as described above and suitable for transformation of plant cells are prepared. Techniques for transforming a wide variety of higher plant species are well known and described in the technical, scientific, and patent literature. See, for example, Weising, et al., (1988) *Ann. Rev. Genet.* 22:421-477. For example, the DNA construct may be introduced directly into the genomic DNA of the plant cell using techniques such as electroporation, polyethylene glycol (PEG), poration, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp. 197-213 in *Plant Cell, Tissue and Organ Culture, Fundamental Methods*, Eds. Gamborg and Phillips. Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using PEG precipitation is described in Paszkowski, et al., (1984) *Embo J.* 3:2717-2722. Electroporation techniques are described in Fromm, et al., (1985) *Proc. Natl. Acad. Sci. (USA)* 82:5824. Ballistic transformation techniques are described in Klein, et al., (1987) *Nature* 327:70-73.

*Agrobacterium tumefaciens*-mediated transformation techniques are well described in the scientific literature. See, for example Horsch, et al., (1984) *Science* 233:496-498 and Fraley, et al., (1983) *Proc. Natl. Acad. Sci. (USA)* 80:4803. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, Rigby, Ed., London, Academic Press, 1987; and Lichtensteinand Draper, In: DNA Cloning, Vol. II, Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman, et al., (1984) *Plant Cell Physiol.* 25:1353), (3) the vortexing method (see, e.g., Kindle, (1990) *Proc. Natl. Acad. Sci., (USA)* 87:1228).

DNA can also be introduced into plants by direct DNA transfer into pollen as described by Zhou, et al., (1983) *Methods in Enzymology* 101:433; Hess, (1987) *Intern Rev. Cytol.,* 107:367; Luo, et al., (1988) *Plant Mol. Biol. Reporter,* 6:165. Expression of polypeptide coding genes can be obtained by injection of the DNA into reproductive organs of a plant as described by Pena, et al., (1987) *Nature,* 325:274. DNA can also be injected directly into the cells of immature embryos and the rehydration of desiccated embryos as described by Neuhaus, et al., (1987) *Theor. Appl. Genet.,* 75:30 and Benbrook, et al., (1986) *In Proceedings Bio Expo* 1986, Butterworth, Stoneham, Mass., pp. 27-54. A variety of plant viruses that can be employed as vectors are known in the art and include cauliflower mosaic virus (CaMV), geminivirus, brome mosaic virus and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics and micro-injection of the DNA directly into the cells. The transfected cells are cultured by means well known in the art. Kuchler, *Biochemical Methods in Cell Culture and Virology*, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3-284 in *The Peptides: Analysis, Synthesis, Biology. Vol. 2: Special Methods in Peptide Synthesis, Part A.*; Merrifield, et al., (1963) *J. Am. Chem. Soc.* 85:2149-2156 and Stewart, et al., (1984) *Solid Phase Peptide Synthesis, 2nd ed.*, Pierce Chem. Co., Rockford, Ill. Proteins of greater length may be synthesized by condensation of the amino and carboxy termini of shorter fragments. Methods of forming peptide bonds by activation of a carboxy terminal end (e.g., by the use of the coupling reagent N,N'-dicyclohexylcarbodiimide) are known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods and others. See, for instance, Scopes, (1982) *Protein Purification: Principles and Practice*, Springer-Verlag: New York; Deutscher, (1990) *Guide to Protein Purification*, Academic Press. For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation Transgenic Plant Regeneration Transformed plant cells which are derived by any of the above transformation techniques can be cultured to regenerate a whole plant which possesses the transformed genotype. Such regeneration techniques often rely on manipulation of certain phytohormones in a tissue culture growth medium. For transformation and regeneration of maize, see, Gordon-Kamm, et al., (1990) *The Plant Cell*, 2:603-618.

Plants cells transformed with a plant expression vector can be regenerated, e.g., from single cells, callus tissue or leaf discs according to standard plant tissue culture techniques. It is well known in the art that various cells, tissues and organs from almost any plant can be successfully cultured to regenerate an entire plant. Plant regeneration from cultured protoplasts is described in Evans, et al., (1983) *Protoplasts Isolation and Culture, Handbook of Plant Cell Culture*, Macmillan Publishing Company, New York, pp. 124-176 and Binding, (1985) *Regeneration of Plants, Plant Protoplasts*, CRC Press, Boca Raton, pp. 21-73.

The regeneration of plants containing the foreign gene introduced by *Agrobacterium* from leaf explants can be achieved as described by Horsch, et al., (1985) *Science*, 227: 1229-1231. In this procedure, transformants are grown in the presence of a selection agent and in a medium that induces the regeneration of shoots in the plant species being transformed as described by Fraley, et al., (1983) *Proc. Natl. Acad. Sci. (U.S.A.)* 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs or parts thereof. Such regeneration techniques are described generally in Klee, et al., (1987) *Ann. Rev. of Plant Phys.* 38:467-486. The regeneration of plants from either single plant protoplasts or various explants is well known in the art. See, for example, *Methods for Plant Molecular Biology*, Weissbach and Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, New York (1994); *Corn and Corn Improvement*, 3$^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit and the like are included in the invention, provided that these parts comprise cells comprising the isolated nucleic acid of the present invention. Progeny and variants and mutants of the regenerated plants are also included within the scope of the invention, provided that these parts comprise the introduced nucleic acid sequences. Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Modulating Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the ratio of the polypeptides of the present invention in a plant. The method comprises introducing into a plant cell a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or the ratios of the polypeptides in the plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling, et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing or PCR analysis using primers specific to the promoter and to the gene and detecting amplicons produced therefrom. A plant or plant part altered or modified by the foregoing embodiments is grown under plant-forming conditions for a time sufficient to modulate the concentration and/or ratios of polypeptides of the present invention in the plant. Plant-forming conditions are well known in the art and discussed briefly, supra.

In general, concentration or the ratios of the polypeptides is increased or decreased by at least 5%, 10%, 20%, 30%, 40%, 50%, 60%, 70%, 80% or 90% relative to a native control plant, plant part or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 7-methylguanosine cap structure (Drummond, et al., (1985) *Nucleic Acids Res.* 13:7375). Negative elements include stable intramolecular 5' UTR stem-loop structures (Muesing et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see, Devereaux, et al., (1984) *Nucleic Acids Res.* 12:387-395) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention and compositions resulting therefrom. Sequence shuffling is described in PCT Publication Number WO 97/20078. See also, Zhang, et al., (1997) *Proc. Natl. Acad. Sci. USA* 94:4504-4509. Generally, sequence shuffling includes the synthetic re-arrangement ("shuffling") of a part or parts of one or more allelic forms of the gene of interest. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence affecting transcription, RNA processing, RNA stability, chromatin conformation, translation or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention and (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla or kingdoms. For example, a polynucleotide having a consensus sequence from a gene family of *Zea mays* can be used to generate antibody or nucleic acid probes or primers to other *Gramineae* species such as wheat, rice or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30 or 40 amino acids in length, or 20, 30, 40, 50, 100 or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001 or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Computer Applications

The present invention provides machines, data structures and processes for modeling or analyzing the polynucleotides and polypeptides of the present invention.

A. Machines and Data Structures

The present invention provides a machine having a memory comprising data representing a sequence of a polynucleotide or polypeptide of the present invention. The machine of the present invention is typically a digital computer. The memory of such a machine includes, but is not limited to, ROM or RAM or computer readable media such as, but not limited to, magnetic media such as computer disks or hard drives or media such as CD-ROM. Thus, the present invention also provides a data structure comprising a sequence of a polynucleotide of the present invention embodied in a computer readable medium. As those of skill in the art will be aware, the form of memory of a machine of the present invention or the particular embodiment of the computer readable medium is not a critical element of the invention and can take a variety of forms.

B. Homology Searches

The present invention provides a process for identifying a candidate homologue (i.e., an ortholog or paralog) of a polynucleotide or polypeptide of the present invention. A candidate homologue has statistically significant probability of having the same biological function (e.g., catalyzes the same reaction, binds to homologous proteins/nucleic acids) as the reference sequence to which it's compared. Accordingly, the polynucleotides and polypeptides of the present invention have utility in identifying homologs in animals or other plant species, particularly those in the family Gramineae such as, but not limited to, sorghum, wheat or rice.

The process of the present invention comprises obtaining data representing a polynucleotide or polypeptide test sequence. Test sequences are generally at least 25 amino acids in length or at least 50 nucleotides in length. Optionally, the test sequence can be at least 50, 100, 150, 200, 250, 300 or 400 amino acids in length. A test polynucleotide can be at least 50, 100, 200, 300, 400 or 500 nucleotides in length. Often the test sequence will be a full-length sequence. Test sequences can be obtained from a nucleic acid of an animal or plant. Optionally, the test sequence is obtained from a plant species other than maize whose function is uncertain but will be compared to the test sequence to determine sequence similarity or sequence identity; for example, such plant species can be of the family Gramineae, such as wheat, rice or sorghum. The test sequence data are entered into a machine, typically a computer, having a memory that contains data representing a reference sequence. The reference sequence can be the sequence of a polypeptide or a polynucleotide of the present invention and is often at least 25 amino acids or 100 nucleotides in length. As those of skill in the art are aware, the greater the sequence identity/similarity between a reference sequence of known function and a test sequence, the greater the probability that the test sequence will have the same or similar function as the reference sequence.

The machine further comprises a sequence comparison means for determining the sequence identity or similarity between the test sequence and the reference sequence. Exemplary sequence comparison means are provided for in sequence analysis software discussed previously. Optionally, sequence comparison is established using the BLAST or GAP suite of programs.

The results of the comparison between the test and reference sequences can be displayed. Generally, a smallest sum probability value (P(N)) of less than 0.1, or alternatively, less than 0.01, 0.001, 0.0001 or 0.00001 using the BLAST 2.0 suite of algorithms under default parameters identifies the test sequence as a candidate homologue (i.e., an allele, ortholog or paralog) of the reference sequence. A nucleic acid comprising a polynucleotide having the sequence of the candidate homologue can be constructed using well known library isolation, cloning or in vitro synthetic chemistry techniques (e.g., phosphoramidite) such as those described herein. In additional embodiments, a nucleic acid comprising a polynucleotide having a sequence represented by the candidate homologue is introduced into a plant; typically, these polynucleotides are operably linked to a promoter. Confirmation of the function of the candidate homologue can be established by operably linking the candidate homolog nucleic acid to, for example, an inducible promoter or by expressing the antisense transcript and analyzing the plant for changes in phenotype consistent with the presumed function of the candidate homolog. Optionally, the plant into which these nucleic acids are introduced is a monocot such as from the family Gramineae. Exemplary plants include maize, sorghum, wheat, rice, canola, alfalfa, cotton and soybean.

C. Computer Modeling

The present invention provides a process of modeling/analyzing data representative of the sequence a polynucleotide or polypeptide of the present invention. The process comprises entering sequence data of a polynucleotide or polypeptide of the present invention into a machine, manipulating the data to model or analyze the structure or activity of the polynucleotide or polypeptide, and displaying the results of the modeling or analysis. A variety of modeling and analytic tools are well known in the art and available from such commercial vendors as Genetics Computer Group (Version 10, Madison, Wis.). Included amongst the modeling/analysis tools are methods to: 1) recognize overlapping sequences (e.g., from a sequencing project) with a polynucleotide of the present invention and create an alignment called a "contig"; 2) identify restriction enzyme sites of a polynucleotide of the present invention; 3) identify the products of a T1 ribonuclease digestion of a polynucleotide of the present invention; 4) identify PCR primers with minimal self-complementarity; 5) compare two protein or nucleic acid sequences and identifying points of similarity or dissimilarity between them; 6) compute pairwise distances between sequences in an alignment, reconstruct phylogenetic trees using distance methods, and calculate the degree of divergence of two protein coding regions; 7) identify patterns such as coding regions, terminators, repeats, and other consensus patterns in polynucleotides of the present invention; 8) identify RNA secondary structure; 9) identify sequence motifs, isoelectric point, secondary structure, hydrophobicity, and antigenicity in polypeptides of the present invention and 10) translate polynucleotides of the present invention and backtranslate polypeptides of the present invention.

Detection of Nucleic Acids

The present invention further provides methods for detecting a polynucleotide of the present invention in a nucleic acid sample suspected of containing a polynucleotide of the present invention, such as a plant cell lysate, particularly a lysate of maize. In some embodiments, a gene of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result. Detection of the hybridization complex can be achieved using any number of well known methods. For example, the nucleic acid sample, or a portion thereof, may be assayed by hybridization formats including but not limited to, solution phase, solid phase, mixed phase or in situ hybridization assays.

Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes, radiolabels, enzymes and colorimetric labels. Other labels include ligands which bind to antibodies labeled with fluorophores, chemiluminescent agents and enzymes. Labeling the nucleic acids of the present invention is readily achieved such as by the use of labeled PCR primers.

Although the present invention has been described in some detail by way of illustration and example for purposes of clarity of understanding, it will be obvious that certain changes and modifications may be practiced within the scope of the appended claims.

EXAMPLES

Example 1

Construction of a cDNA Library

Total RNA can be isolated from maize tissues with TRIzol Reagent (Life Technology Inc. Gaithersburg, Md.) using a modification of the guanidine isothiocyanate/acid-phenol procedure described by Chomczynski and Sacchi (Chomczynski and Sacchi, (1987) *Anal. Biochem.* 162:156). In brief, plant tissue samples are pulverized in liquid nitrogen before the addition of the TRIzol Reagent and then further homogenized with a mortar and pestle. Addition of chloroform followed by centrifugation is conducted for separation of an aqueous phase and an organic phase. The total RNA is recovered by precipitation with isopropyl alcohol from the aqueous phase.

The selection of poly(A)+ RNA from total RNA can be performed using PolyATact system (Promega Corporation. Madison, Wis.). Biotinylated oligo(dT) primers are used to hybridize to the 3' poly(A) tails on mRNA. The hybrids are captured using streptavidin coupled to paramagnetic particles and a magnetic separation stand. The mRNA is then washed at high stringency conditions and eluted by RNase-free deionized water.

cDNA synthesis and construction of unidirectional cDNA libraries can be accomplished using the SuperScript Plasmid System (Life Technology Inc. Gaithersburg, Md.). The first strand of cDNA is synthesized by priming an oligo(dT) primer containing a Not I site. The reaction is catalyzed by SuperScript ReverseTranscriptase II at 45° C. The second strand of cDNA is labeled with alpha-$^{32}$P-dCTP and a portion of the reaction analyzed by agarose gel electrophoresis to determine cDNA sizes. cDNA molecules smaller than 500 base pairs and unligated adapters are removed by Sephacryl-S400 chromatography. The selected cDNA molecules are ligated into pSPORT1 vector in between of Not I and Sal I sites.

Alternatively, cDNA libraries can be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see, Adams, et al., (1991) *Science* 252:1651-1656). The resulting ESTs are analyzed using a Perkin Elmer Model 377 fluorescent sequencer.

Example 2

Construction of a Full-length Enriched cDNA Library

An enriched full-length cDNA library can be constructed using one of two variations of the method of Carninci, et al., (1996) *Genomics* 37:327-336. These variations are based on chemical introduction of a biotin group into the diol residue of the 5' cap structure of eukaryotic mRNA to select full-length first strand cDNA. The selection occurs by trapping the biotin residue at the cap sites using streptavidin-coated magnetic beads followed by RNase I treatment to eliminate incompletely synthesized cDNAs. Second strand cDNA is synthesized using established procedures such as those provided in Life Technologies' (Rockville, Md.) "SuperScript Plasmid System for cDNA Synthesis and Plasmid Cloning" kit. Libraries made by this method have been shown to contain 50% to 70% full-length cDNAs.

The first strand synthesis methods are detailed below. An asterisk denotes that the reagent was obtained from Life Technologies, Inc.

A. First Strand cDNA Synthesis Method 1 (with Trehalose)

| | |
|---|---|
| mRNA (10 ug) | 25 µl |
| *Not I primer (5 ug) | 10 µl |

-continued

| | |
|---|---|
| *5x 1$^{st}$ strand buffer | 43 µl |
| *0.1m DTT | 20 µl |
| *dNTP mix 10 mm | 10 µl |
| BSA 10 ug/µl | 1 µl |
| Trehalose (saturated) | 59.2 µl |
| RNase inhibitor (Promega) | 1.8 µl |
| *Superscript II RT 200 u/µl | 20 µl |
| 100% glycerol | 18 µl |
| Water | 7 µl |

The mRNA and Not I primer are mixed and denatured at 65° C. for 10 min. They are then chilled on ice and other components added to the tube. Incubation is at 45° C. for 2 min. Twenty microliters of RT (reverse transcriptase) is added to the reaction and start program on the thermocycler (MJ Research, Waltham, Mass.):

| | | |
|---|---|---|
| Step 1 | 45° C. | 10 min |
| Step 2 | 45° C. | −0.3° C./cycle, 2 seconds/cycle |
| Step 3 | | go to 2 for 33 cycles |
| Step 4 | 35° C. | 5 min |
| Step 5 | 45° C. | 5 min |
| Step 6 | 45° C. | 0.2° C./cycle, 1 sec/cycle |
| Step 7 | | go to 7 for 49 cycles |
| Step 8 | 55° C. | 0.1° C./cycle, 12 sec/cycle |
| Step 9 | | go to 8 for 49 cycles |
| Step 10 | 55° C. | 2 min |
| Step 11 | 60° C. | 2 min |
| Step 12 | | go to 11 for 9 times |
| Step 13 | 4° C. | forever |
| Step 14 | | end |

B. First Strand cDNA Synthesis Method 2

| | |
|---|---|
| mRNA (10 µg) | 25 µl |
| water | 30 µl |
| *Not I adapter primer (5 µg) | 10 µl |
| 65° C. for 10 min, chill on ice, then add following reagents, | |
| *5x first buffer | 20 µl |
| *0.1 M DTT | 10 µl |
| *10 mM dNTP mix | 5 µl |

Incubate at 45° C. for 2 min, then add 10 µl of *Superscript II RT (200 u/µl), start the following program:

| | | |
|---|---|---|
| Step 1 | 45° C. | for 6 sec, −0.1° C./cycle |
| Step 2 | | go to 1 for 99 additional cycles |
| Step 3 | 35° C. | for 5 min |
| Step 4 | 45° C. | for 60 min |
| Step 5 | 50° C. | for 10 min |
| Step 6 | 4° C. | forever |
| Step 7 | | end |

After the 1$^{st}$ strand cDNA synthesis, the DNA is extracted by phenol according to standard procedures, and then precipitated in NaOAc and ethanol, and stored in −20° C.

C. Oxidization of the Diol Group of mRNA for Biotin Labeling

First strand cDNA is spun down and washed once with 70% EtOH. The pellet resuspended in 23.2 µl of DEPC treated water and put on ice. Prepare 100 mM of NaIO$_4$ freshly, and then add the following reagents:

| | |
|---|---|
| mRNA: 1ˢᵗ cDNA (start with 20 μg mRNA) | 46.4 μl |
| 100 mM NaIO$_4$ (freshly made) | 2.5 μl |
| NaOAc 3M pH 4.5 | 1.1 μl |

To make 100 mM NaIO$_4$, use 21.39 μg of NaIO$_4$ for 1 μl of water.
Wrap the tube in a foil and incubate on ice for 45 min.
After the incubation, the reaction is then precipitated in:

| | |
|---|---|
| 5M NaCl | 10 μl |
| 20% SDS | 0.5 μl |
| isopropanol | 61 μl |

Incubate on ice for at least 30 min, then spin it down at max speed at 4° C. for 30 min and wash once with 70% ethanol and then 80% EtOH.
D. Biotinylation of the mRNA Diol Group
Resuspend the DNA in 110 μl DEPC treated water, then add the following reagents:

| | |
|---|---|
| 20% SDS | 5 μl |
| 2M NaOAc pH 6.1 | 5 μl |
| 10 mm biotin hydrazide (freshly made) | 300 μl |

Wrap in a foil and incubate at room temperature overnight.
E. RNase I Treatment
Precipitate DNA in:

| | |
|---|---|
| 5M NaCl | 10 μl |
| 2M NaOAc pH 6.1 | 75 μl |
| biotinylated mRNA:cDNA | 420 μl |
| 100% EtOH (2.5 Vol) | 1262.5 μl |

(Perform this precipitation in two tubes and split the 420 μl of DNA into 210 μl each, add 5 μl of 5M NaCl, 37.5 μl of 2M NaOAc pH 6.1 and 631.25 μl of 100% EtOH).
Store at −20° C. for at least 30 min. Spin the DNA down at 4° C. at maximal speed for 30 min. and wash with 80% EtOH twice, then dissolve DNA in 70 μl RNase free water. Pool two tubes and end up with 140 μl.
Add the following reagents:

| | |
|---|---|
| RNase One 10 U/μl | 40 μl |
| 1ˢᵗ cDNA:RNA | 140 μl |
| 10X buffer | 20 μl |

Incubate at 37° C. for 15 min.
Add 5 μl of 40 μg/μl yeast tRNA to each sample for capturing.
F. Full Length 1ˢᵗ cDNA Capturing
Blocking the beads with yeast tRNA:

| | |
|---|---|
| Beads | 1 ml |
| Yeast tRNA 40 μg/μl | 5 μl |

Incubate on ice for 30 min with mixing, wash 3 times with 1 ml of 2M NaCl, 50 mm EDTA, pH 8.0.

Resuspend the beads in 800 μl of 2M NaCl, 50 mm EDTA, pH 8.0, add RNase I treated sample 200 μl, and incubate the reaction for 30 min at room temperature.
Capture the beads using the magnetic stand, save the supernatant, and start following washes:
2 washes with 2M NaCl, 50 mm EDTA, pH 8.0, 1 ml each time,
1 wash with 0.4% SDS, 50 μg/ml tRNA,
1 wash with 10 mm Tris-Cl pH 7.5, 0.2 mm EDTA, 10 mm NaCl, 20% glycerol,
1 wash with 50 μg/ml tRNA,
1 wash with 1ˢᵗ cDNA buffer
G. Second Strand cDNA Synthesis
Resuspend the beads in:

| | |
|---|---|
| *5X first buffer | 8 μl |
| *0.1 mM DTT | 4 μl |
| *10 mm dNTP mix | 8 μl |
| *5× 2nd buffer | 60 μl |
| *E. coli Ligase 10 U/μl | 2 μl |
| *E. coli DNA polymerase 10 U/μl | 8 μl |
| *E. coli RNaseH 2 U/μl | 2 μl |
| P32 dCTP 10 μci/μl | 2 μl |
| Or water up to 300 μl | 208 μl |

Incubate at 16° C. for 2 hr with mixing the reaction in every 30 min. Add 4 μl of T4 DNA polymerase and incubate for additional 5 min at 16° C.
Elute 2ⁿᵈ cDNA from the beads.
Use a magnetic stand to separate the 2ⁿᵈ cDNA from the beads, then resuspend the beads in 200 μl of water and then separate again, pool the samples (about 500 μl), Add 200 μl of water to the beads, then 200 μl of phenol:chloroform, vortex and spin to separate the sample with phenol.
Pool the DNA together (about 700 μl) and use phenol to clean the DNA again, DNA is then precipitated in 2 μg of glycogen and 0.5 vol of 7.5M NH4OAc and 2 vol of 100% EtOH. Precipitate overnight. Spin down the pellet and wash with 70% EtOH, air-dry the pellet.

| | | | |
|---|---|---|---|
| DNA | 250 μl | DNA | 200 μl |
| 7.5M NH4OAc | 125 μl | 7.5M NH4OAc | 100 μl |
| 100% EtOH | 750 μl | 100% EtOH | 600 μl |
| glycogen 1 μg/μl | 2 μl | glycogen 1 μg/μl | 2 μl |

H. Sal I Adapter Ligation
Resuspend the pellet in 26 μl of water and use 1 μl for TAE gel.
Set up reaction as following:

| | |
|---|---|
| 2ⁿᵈ strand cDNA | 25 μl |
| *5X T4 DNA ligase buffer | 10 μl |
| *Sal I adapters | 10 μl |
| *T4 DNA ligase | 5 μl |

Mix gently, incubate the reaction at 16° C. overnight.
Add 2 μl of ligase second day and incubate at room temperature for 2 hrs (optional).
Add 50 μl water to the reaction and use 100 μl of phenol to clean the DNA, 90 μl of the upper phase is transferred into a new tube and precipitate in:

| | |
|---|---|
| Glycogen 1 µg/µl | 2 µl |
| Upper phase DNA | 90 µl |
| 7.5M NH4OAc | 50 µl |
| 100% EtOH | 300 µl | precipitate at −20° C. overnight
Spin down the pellet at 4° C. and wash in 70% EtOH, dry the pellet.
I. Not I Digestion

| | |
|---|---|
| 2$^{nd}$ cDNA | 41 µl |
| *Reaction 3 buffer | 5 µl |
| *Not I 15 u/µl | 4 µl |

Mix gently and incubate the reaction at 37° C. for 2 hr.
Add 50 µl of water and 100 µl of phenol, vortex, and take 90 µl of the upper phase to a new tube, then add 50 µl of NH40Ac and 300 µl of EtOH. Precipitate overnight at −20° C.
Cloning, ligation and transformation are performed per the Superscript cDNA synthesis kit.

Example 3 cDNA Sequencing and Library Subtraction

Individual colonies can be picked and DNA prepared either by PCR with M13 forward primers and M13 reverse primers, or by plasmid isolation. cDNA clones can be sequenced using M13 reverse primers.

cdNA libraries are plated out on 22×22 cm$^2$ agar plate at density of about 3,000 colonies per plate. The plates are incubated in a 37° C. incubator for 12-24 hours. Colonies are picked into 384-well plates by a robot colony picker, Q-bot (GENETIX Limited). These plates are incubated overnight at 37° C. Once sufficient colonies are picked, they are pinned onto 22×22 cm$^2$ nylon membranes using Q-bot. Each membrane holds 9,216 or 36,864 colonies. These membranes are placed onto an agar plate with an appropriate antibiotic. The plates are incubated at 37° C. overnight.

After colonies are recovered on the second day, these filters are placed on filter paper prewetted with denaturing solution for four minutes, then incubated on top of a boiling water bath for an additional four minutes. The filters are then placed on filter paper prewetted with neutralizing solution for four minutes. After excess solution is removed by placing the filters on dry filter papers for one minute, the colony side of the filters is placed into Proteinase K solution, incubated at 37° C. for 40-50 minutes. The filters are placed on dry filter papers to dry overnight. DNA is then cross-linked to nylon membrane by UV light treatment.

Colony hybridization is conducted as described by Sambrook, Fritsch and Maniatis, (in Molecular Cloning: A laboratory Manual, 2$^{nd}$ Edition). The following probes can be used in colony hybridization:

1. First strand cDNA from the same tissue as the library was made from to remove the most redundant clones.
2. 48-192 most redundant cDNA clones from the same library based on previous sequencing data.
3. 192 most redundant cDNA clones in the entire maize sequence database.
4. A Sal-A20 oligo nucleotide: SEQ ID NO: 15: TCG ACC CAC GCG TCC GAA AAA AAA AAA AAA AAA, removes clones containing a poly A tail but no cDNA.
5. cDNA clones derived from rRNA.

The image of the autoradiography is scanned into computer and the signal intensity and cold colony addresses for each colony is analyzed. Re-arraying of cold-colonies from 384 well plates to 96 well plates is conducted using Q-bot.

Example 4

Identification of the Gene from a Computer Homology Search

Gene identities can be determined by conducting BLAST (Basic Local Alignment Search Tool; Altschul, et al., (1993) *J. Mol. Biol.* 215:403-410; searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences are analyzed for similarity to all publicly available DNA sequences contained in the "nr" database using the BLASTN algorithm. The DNA sequences are translated in all reading frames and compared for similarity to all publicly available protein sequences contained in the "nr" database using the BLASTX algorithm (Gish and States, (1993) *Nature Genetics* 3:266-272) provided by the NCBI. In some cases, the sequencing data from two or more clones containing overlapping segments of DNA are used to construct contiguous DNA sequences.

Sequence alignments and percent identity calculations can be performed using the Megalign program of the LASERGENE bioinformatics computing suite (DNASTAR Inc., Madison, Wis.). Multiple alignment of the sequences can be performed using the Clustal method of alignment (Higgins and Sharp, (1989) *CABIOS.* 5:151-153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

Example 5

Expression of Transgenes in Monocot Cells

A transgene comprising a cDNA encoding the instant polypeptides in sense orientation with respect to the maize 27 kD zein promoter that is located 5' to the cDNA fragment and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209) and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue; Stratagene). Bacterial transformants can be screened by restriction enzyme digestion of plasmid DNA and limited nucleotide sequence analysis using the dideoxy chain termination method (Sequenase DNA Sequencing Kit; US Biochemical). The resulting plasmid construct would comprise a transgene encoding, in the 5' to 3' direction, the maize 27 kD zein promoter, a cDNA fragment encoding the instant polypeptides and the 10 kD zein 3' region.

The transgene described above can then be introduced into maize cells by the following procedure. Immature maize embryos can be dissected from developing caryopses derived from crosses of the inbred maize lines H99 and LH132. The embryos are isolated 10 to 11 days after pollination when they are 1.0 to 1.5 mm long. The embryos are then placed with the axis-side facing down and in contact with agarose-solidified N6 medium (Chu, et al., (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (Hoechst Ag, Frankfurt, Germany) or equivalent may be used in transformation experiments in order to provide for a selectable marker. This plasmid contains the Pat gene (see, European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell, et al., (1985) *Nature* 313:810-812) and the 3' region of the nopaline synthase gene from the T-DNA of the Ti plasmid of *Agrobacterium tumefaciens*.

The particle bombardment method (Klein, et al., (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton flying disc (Bio-Rad Labs). The particles are then accelerated into the maize tissue with a Biolistic PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm, et al., (1990) *Bio/Technology* 8:833-839).

Example 6

Expression of Transgenes in Dicot Cells

A seed-specific expression cassette composed of the promoter and transcription terminator from the gene encoding the β subunit of the seed storage protein phaseolin from the bean *Phaseolus vulgaris* (Doyle, et al., (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos, which produce secondary embryos are then excised and placed into a suitable liquid medium. After repeated selection for clusters of somatic embryos, which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein, et al., (1987) *Nature* (London) 327:70-73, U.S. Pat. No. 4,945,050). A Du Pont Biolistic PDS1000/HE instrument (helium retrofit) can be used for these transformations.

A selectable marker gene which can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium* tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µl), 20 µl spermidine (0.1 M) and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of a Transgene in Microbial Cells

The cDNAs encoding the instant polypeptides can be inserted into the T7 E. coli expression vector pBT430. This vector is a derivative of pET-3a (Rosenberg, et al., (1987) Gene 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG low melting agarose gel (FMC). Buffer and agarose contain 10 µg/ml ethidium bromide for visualization of the DNA fragment. The fragment can then be purified from the agarose gel by digestion with GELase (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier, et al., (1986) J. Mol. Biol. 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One microgram of protein from the soluble fraction of the culture can be separated by SDS-polyacrylamide gel electrophoresis. Gels can be observed for protein bands migrating at the expected molecular weight.

Example 8

Phylogenetic Analysis of MADS Box Proteins Encoded by Maize Genes—FTM1, 2, 3 and SVP1, 2, 3

A phylogenetic analysis of the FTM and SVP proteins was made using Genetics Computer Group's (Madison, Wis.) PILEUP software, Vector NTI's (North Bethesda, Md.) ALIGNX. Various suppliers of sequence-analysis software are listed in chapter 7 of Current Protocols in Molecular Biology, Ausubel, et al., Eds., Current Protocols, a joint venture between Greene Publishing Associates, Inc. and John Wiley & Sons, Inc. (Supplement 30). These methods allow similar polynucleotides to be aligned and a consensus or generic sequence generated using the multiple sequence alignment software. The phylogenic analysis of the MADS box genes is found in FIG. 1.

MADS-box genes belong to a large family of regulatory genes that possess a characteristic DNA binding domain, MADS-box. Members of this gene family display primarily floral-specific expression and play important roles in plant development. Phylogenetic analysis demonstrates that members of the plant MADS-box gene family are organized into a dozen distinct gene groups (clades), which reflect the true phylogeny of the MADS box gene families and their functional similarity (Theissen, et al., (1996) J Mol Evol. 43:484-516). Phylogenetic analysis of novel MADS box genes, SVP's and FTM's delimits them into three separate clades, SQUAMOSA-like (FTM1,2), AGL2-like (FTM3), and SVP-like (SVP1,2,3) (FIG. 1).

SQUAMOSA-like MADS-box genes determine the identity of the floral meristems (Klein, et al., (1996) *Mol Gen Genet.* 250:7-16; Theissen, et al., (1996) *J Mol Evol.* 43:484-5160). However, in petunia the MADS box gene PFG (petunia flowering gene) controls the transition from vegetative to reproductive development (Immink, et al., (1999) *Development* 126:5117-5126). Thus, members of the SQUAMOSA clade may function as flowering-time genes.

FTM3 belongs to the agl2 (agamous-like 2) clade. The function of this group is less defined and very divergent. Potential activities as mediators between the floral meristem and floral organ identity genes (Theissen, et al., (1996) *J Mol Evol.* 43:484-5160) are probable. FTM3 gene is highly expressed in silks, suggesting its possible role in silk development.

SVP genes form a clear clade with the *Arabidopsis* SVP gene (Hartmann, et al., (2000) *Plant Journal* 21:351-360) and agl24 genes (agamous-like 24) (Yu, et al., (2002) *PNAS* 99:16336-16341). The SVP gene is a dosage dependent repressor of flowering in *arabidopsis*. AGL24 gene works in an opposite manner, as a dosage dependent mediator of flowering in *arabidopsis* (Yu, et al., (2002) *PNAS* 99:16336-16341). Thus members of the SVP clade control flowering time in *arabidopsis*. Maize SVP 1, 2, 3 genes demonstrate a pattern of expression similar to the *arabidopsis* SVP genes, such as expression in vegetative tissues and absence of expression in the generative tissues. The shared evolutionary history, which appears to reflect distinct functional roles of MADS families in flower development, supports the function of SVP genes as negative regulators and FTM genes as positive regulators of flowering time in maize.

Example 9

Expression of FTM and SVP Genes in Different Plant Tissues

To validate roles of FTM and SVP genes in the transition from vegetative to reproductive growth, their expression profiles have been determined by BLAST analysis of the LYNX MPSS expression database (Pioneer/Dupont proprietary database). MPSS (massively parallel signature sequencing) technology generates 17-mer sequence tags of millions of cDNA molecules, which are in vitro cloned on microbeads (Brenner, et al., (2000) *Nat Biotechnol* 18:630-634; Brenner, et al., (2000) *Proc Natl Acad Sci* 97:1665-1670). The technique provides an unprecedented depth and sensitivity of mRNA detection, including very low expressed messages. The MPSS profiling database is searchable by BLAST to identify gene specific 17-mer tags.

TABLE 1

17-mer TAG sequences

| | |
|---|---|
| SVP1-GATCGGTTAACCTGATT | SEQ ID: 16 |
| SVP2-GATCAGTTAACCTGATT, | SEQ ID: 17 |
| SVP3-GATCGGGAAGACCCAAG | SEQ ID: 18 |
| FTM1-GATCGCGAGAAGCAGCA | SEQ ID: 19 |
| FTM2-GATCGCGAGAGCAGCAG | SEQ ID: 20 |
| FTM3-GATCGCTACGAGTCCTG | SEQ ID: 21 |

Figure 2:
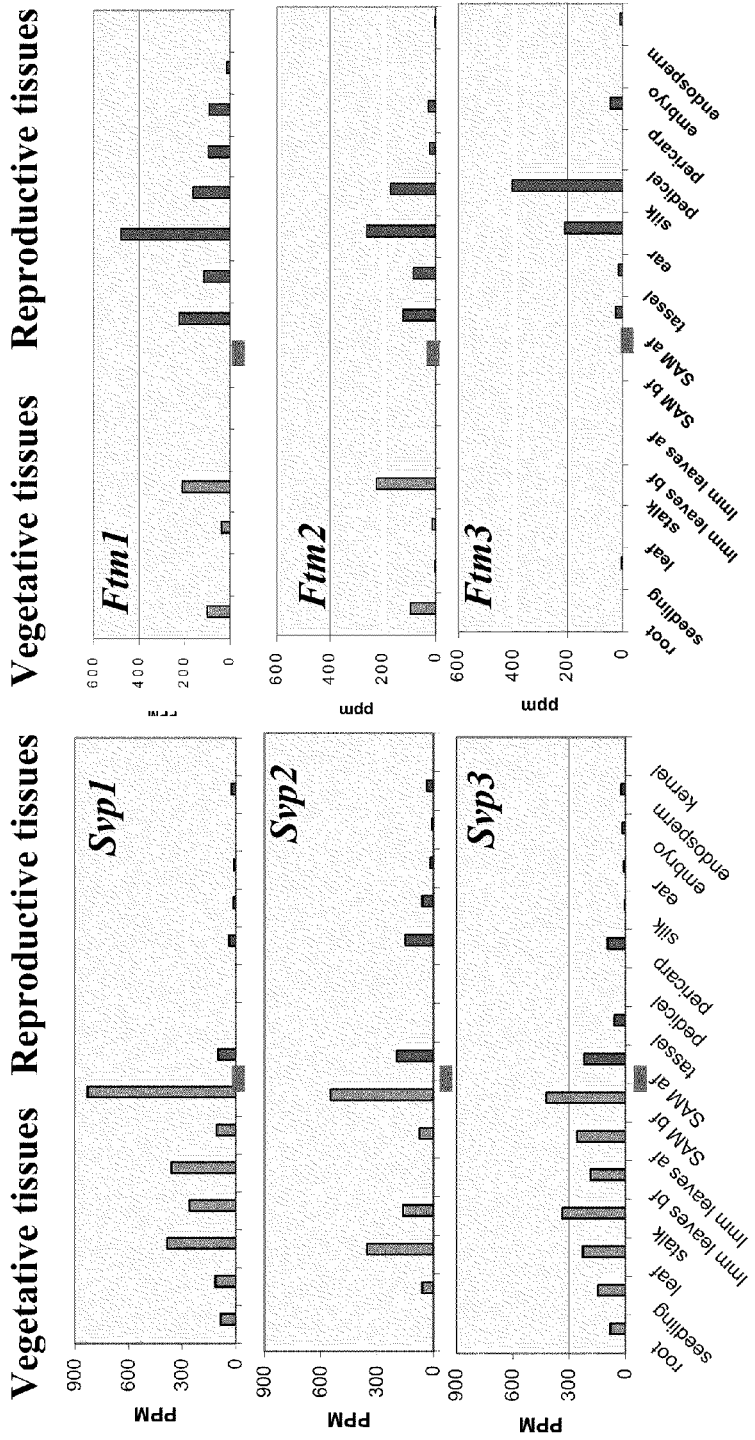
FIG. 2 provides an expression pattern of MADS genes related to flowering. TAGs distribution was analyzed across different plant tissues representing all organs of the corn plant. All SVP genes have a very similar pattern of expression. The expression patterns of FTMs genes are opposite to SVPs. FTM TAG distributions in LYNX database indicate that FTM genes are expressed in reproductive, not vegetative tissues.

The distribution pattern of TAGs was analyzed across different plant tissues, which represent all organs of the corn plant. All SVP genes have a very similar pattern of expression (FIG. 2). They are expressed in all vegetative tissues, including leaves, roots, stems, stalks, seedlings and the shoot apical meristem before the floral transition. SVP TAGs are not detected in reproductive tissues, such as ears, silk, tassels or kernels. Transcription of SVP genes is reduced by 3-8 times in the shoot apical meristems (SAM) after switching to reproductive development. During further meristem development into inflorescence, transcription of SVP genes is reduced to a non-detectable level. These results were confirmed by RT-PCR. The SVP gene expression pattern is similar to the expression pattern of the *arabidopsis* SVP gene, which is a repressor of flowering (Hartmann, et al., (2000) *Plant J.* 21:351-360). Expression patterns of maize SVP genes are consistent with their function as flowering repressors.

Expression patterns of FTM genes are opposite of SVP genes. FTM TAG distributions in the LYNX database indicate that FTM genes are expressed in reproductive, not vegetative tissues (FIG. 2). TAGs are not detected in seedlings, leaves and the shoot apical meristem. A low level of expression is found in root and stalk meristems, suggesting that FTM genes may be active in different meristem tissues. In the shoot apical meristem there are no TAGs for FTM genes, but they appeared sharply in the early stages of the floral transition. RT-PCR demonstrates a low level expression of FTMs in the shoot apical meristems before the transition, and significant activation during and after the transition, to reproductive development of the meristem. The FTM3 gene is more active in silks, which suggests its role in silk development. Expression patterns of maize FTM genes are consistent with their function as flowering activators.

Example 10

Map Position of FTM and SVP Genes and Correlation with QTL's for Flowering Time

FTM and SVP genes have been mapped to chromosomes using the maize-oat addition lines (Kynast, et al., (2001) *Plant Physiol.* 125:1216-27). Pairs of gene-specific primers (Table 2) were designed to amplify each gene from the 10 samples of the oat DNA each of which carried a single maize chromosome. FTM genes were mapped to the following chromosomes: FTM1—chromosome 1, FTM2—chromosome 5, FTM3—chromosome 5, SVP1—chromosome 4, SVP2—chromosome 5, SVP3—chromosome 1.

To correlate genes with flowering QTL's, FTM-SVP genes were mapped using the mapping population SX19 SYN4 derived from B37 and Mo17. Genes can be mapped only in the case of detectable polymorphism in the nucleotide sequences. Using nucleotide polymorphism the following genes were mapped to the specific chromosome locations on the IBM public map. FTM2 and FTM3 are tightly linked to each other and mapped to marker npi282a on chromosome 5. SVP1 is linked to marker umc1775, chromosome 4. SVP3 is linked to markers npi411 and lim504 on chromosome 1. This position corresponds to the flowering QTL identified by Koester, et al., (1993) *Crop Science* 33:1209-1216. Thus, SVP3 is a candidate gene for flowering QTL on a short arm of chromosome 3.

Example 11

Genomic Sequences of Maize FTM1, 2, 3 and SVP1, 2, 3 Genes

Figure 3:
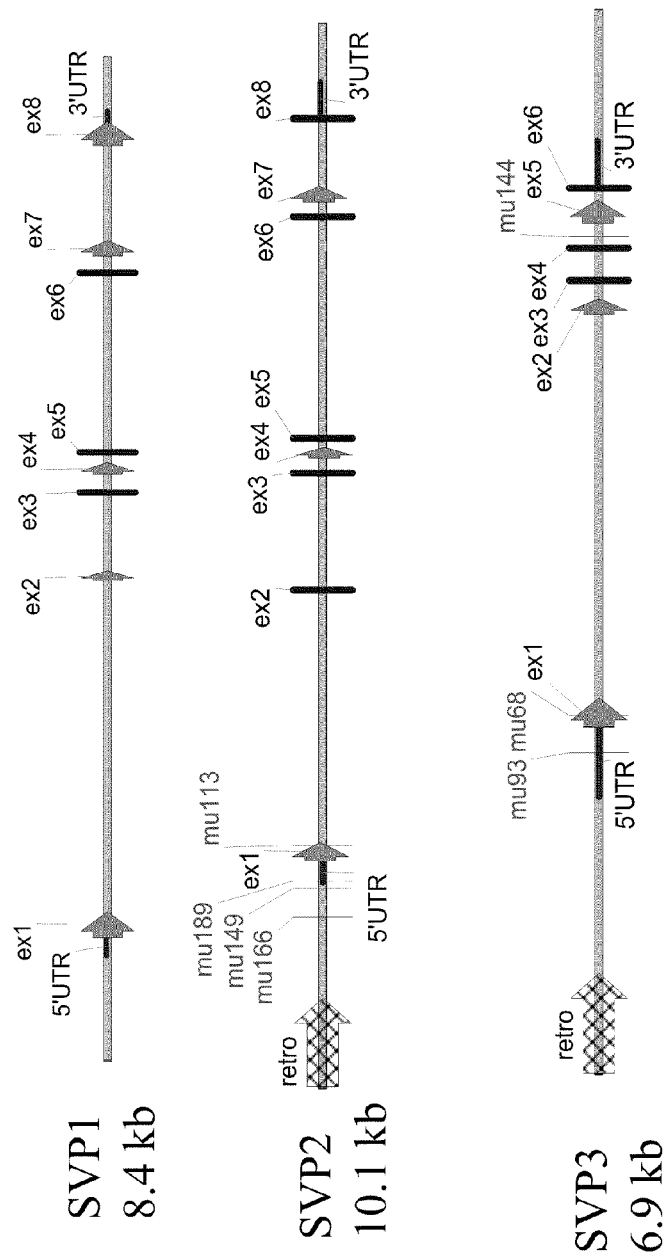
FIG. 3 provides SVP genomic structures. The gene sizes ranged from 6.9-10.1 kb, which are average for plant genes. Genomic structures of SVP1 and 2 genes are very similar, comprising 8 exons and 7 introns FIG. 4 provides genomic structures for FTM. All three FTM genes are composed of 8 exons of identical sizes, which are produced as cDNA of 1.4-1.5 kb. Overall FTM1 and FTM2 genomic sequences across exons and introns share greater than 70% homology indicating that they are recently duplicated genes in the maize genome. However the entire sizes of the genic regions including introns are 41 kb for FTM1; 20.5 kb for FTM2 and 10 kb for FTM3. FTM2 and FTM3 genes are linked to each other being separated only by one retro element.
Figure 4:
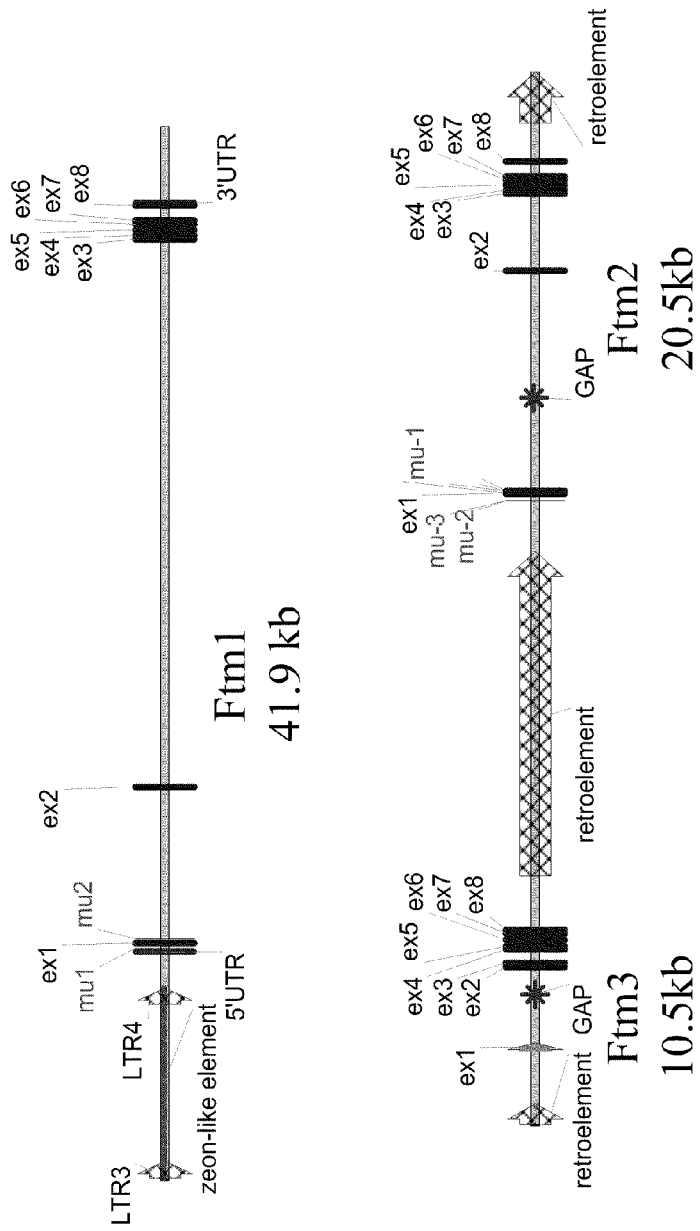

Genomic sequences of FTM-SVP genes were obtained by screening BAC (bacterial artificial chromosome) libraries with inserts of EST's SEQ ID NO: 1, 3, 5, 7, 9. BAC's were sequenced by a shot-gun approach at DuPont sequencing facilities. Genomic structures are shown in FIGS. 3 and 4. The gene sizes range from 6.9-10.1 kb, which are average for plant genes (FIG. 3). Genomic structures of SVP1 and 2 genes are very similar, comprised of 8 exons and 7 introns (FIG. 3). Overall genomic sequences of these two genes across exons and introns share greater than 70% homology, which indicates that they are recently duplicated genes in the maize genome. The SVP3 gene structure is significantly different and shows no nucleotide homology to SVP1 and 2. Nevertheless, at the amino acid levels those proteins share common domains and phylogenetically are very closely related.

All three FTM genes are composed of 8 exons of identical size, which produce cDNA of 1.4-1.5 kb (FIG. 4). Overall FTM1 and FTM2 genomic sequences across exons and introns share greater than 70% homology, indicating that they are recently duplicated genes in the maize genome. However the entire sizes of the genic regions including introns are 41 kb for FTM1; 20.5 kb for FTM2; and 10 kb for FTM3 (FIG. 4). FTM genes are exceptionally large among known plant genes. These huge sizes are created by the $1^{st}$ and $2^{nd}$ introns, which range from 10 kb up to 30 kb. Exons 3 through 8 are divided by small introns 100-200 nt long. These unusual genomic structures suggest that $1^{st}$ and $2^{nd}$ introns are involved in regulation of MADS FTM gene expression. Most likely, they play a role in repression of the FTM genes at the vegetative stage through epigenetic silencing.

Example 12

Inactivation of FTM1, 2 and SVP2, 3 Genes by the Mutator Transposon Insertions

As a method of confirming the function of FTM and SVP genes in flowering time, each genes inactivation was achieved. Pioneer proprietary system TUSC (Trait Utility System for Corn) was used to screen FTM and SVP genes disrupted by the Mutator transposable element insertion. $F_2$ families segregating for the Mutator insertions were screened by PCR with the Mu specific primer (SEQ ID NO: 22) and gene specific primers SEQ ID NO: 23, 24, 25 and 26. Positive signals were found for the Mutator insertions in FTM1, FTM2, SVP2, SVP3. No TUSC alleles were found for the SVP1 gene. Mu insertion sites were identified by sequencing PCR products. Results are summarized in Table 3. All the genes have at least one Mu insertion into protein-coding exons, which should produce the gene knock-outs.

TABLE 2

Primer Sequences for FTM and SVP
SEQ ID 22 >mutator primer
AGAGAAGCCAACGCCAWCGCCTCYATTTCGTC

| | | |
|---|---|---|
| SEQ ID 23 >FTM1 TUSC primer | GGTTTCGACCGTACGAGGAAAGACC | |
| SEQ ID 24 >FTM2 TUSC primer | TATACCATGTGGTGCGGCCACAGGT | |
| SEQ ID: 25 >SVP2 TUSC primer | TTCGCGGGGATCATGTGGGTAATCG | |
| SEQ ID: 26 >SVP3 TUSC primer | AGTAGGCAGTTCCTCACTGGTCCTTTGCG | |

TABLE 3

Description of TUSC alleles of FTM1, 2 and SVP2, 3

| Gene | TUSC pool | Allele name | Site of Mu-insertion |
|---|---|---|---|
| FTM1 | PV03 113 F-07 | ftm1-m1 | 5'UTR |
| | PV03 46 E-10 | ftm1-m2 | exon 1 |
| FTM2 | PV03 78 E-12 | ftm2-m1 | exon 1 |
| | PV03 103 F-10 | ftm2-m2 | exon 1 |
| | PV03 54 D-02 | ftm2-m3 | exon 1 |
| SVP2 | PV03 113 G-01 | mu113 | exon1 |
| | BT94 166 G-08 | mu166 | 5'UTR |
| | PV03 149 A-10 | mu149 | 5'UTR |
| | PV03 189 H-07 | mu189 | 5'UTR |
| SVP3 | PV03 68 C-07 | mu68 | exon1 |
| | PV03 93 D-08 | mu93 | 5'UTR |
| | PV03 144 E-03 | mu144 | intron 4 |

Example 13

Inactivation of FTM3 Genes by the Mutator Transposon Insertions

Confirmation of the function of FTM3, was achieved by inactivation of the gene. The Pioneer proprietary system TUSC (Trait Utility System for Corn) was used to screen FTM3 disrupted by the Mutator transposable element insertion. $F_2$ families segregating for the Mutator insertions were screened by PCR with the Mu specific primer (SEQ ID NO: 22) and gene specific primers SEQ ID NO: 27 and 28. Positive signals were found for the Mutator insertions in FTM3. Mu insertion sites were identified by sequencing PCR products. Results are summarized in Table 4. All alleles have Mu-insertions into 5'UTR. Potential phenotypic changes in plants having the inactivation include plants having delayed flowering and those plants having altered ear development and silk production.

TABLE 4

Description of TUSC alleles of FTM3 gene

| Gene | TUSC pool | Allele name | Site of Mu-insertion |
|---|---|---|---|
| FTM3 | PV03 6 D-08 | ftm3-6D | 5'UTR |
| | PV03 38 A-05 | ftm3-38A | 5'UTR |
| | PV03 38 E-02 | ftm3-38E | 5'UTR |
| | PV03 46 H-02 | ftm3-46H | 5'UTR |

The associated FTM TUSC primers employed were:

SEQ ID 27
>FTM3 TUSC primer  ACTCTTCACCGGTCCAGCTAGTAAATGC

SEQ ID 28
>FTM2 TUSC primer  CATACATGTATCGACCTCCTGCTCGCTT

Example 14

Expression of FTM and SVP Genes in the Shoot Apical Meristems (SAM) and Immature Leaves During Vegetative and Reproductive Seedling Growth To investigate the function of FTM1, 2, 3 and SVP1, 2, 3 in the floral transition expression, analysis by quantitative RT-PCR (QRT-PCR) was conducted on RNA samples isolated from the shoot apical meristems and immature leaves. These tissues are important in determining flowering time. Immature leaves are responsible for generating the flower-inducing signal florigen (Colasanit, et al., (1998) *Cell* 93:593-603). The shoot apical meristem is the organ where transition from the vegetative to reproductive development occurs. Tissues were collected from the greenhouse grown seedlings at 7 days after germination through the floral transition and up to one week after flowering. Three genetic backgrounds were used: wild type (a public line B73), flowering mutants ID1 (indeterminate 1) and dlf (delay flowering). QRT-PCR analyses were set up for each gene with gene-specific primers using the maize ubiquitin gene for normalization. FTM1 and 2 sequences were found to be quite closely related, therefore their expression was tested with the same set of primers. The FTM3 sequence is different from FTM1 and 2, so individual primers were developed for this gene. FTM1, 2 and 3 are expressed in the SAM at the basal level during vegetative stages but their transcription level increases sharply during the transition and declines a week later following the transition from vegetative to reproductive development. The correlation between the level of FTM1, 2 and 3 gene expression suggests that they are positive regulators (activators) of flowering time in maize. However, the function of the FTM3 gene may be different than FTM1 and 2 because they belong to different clades of MADS genes (see, Example 8). Also FTM3 is expressed more strongly during the vegetative stage. FTM1, 2 and 3 genes are expressed in the immature leaves in a similar manner, being at a low level of expression at the vegetative stage and then activated sharply during the floral transition. However, the expression stays at high level after the floral transition in the immature and green leaves, suggesting their contribution to the formation of adult leaf tissues. FTM1 and 2 are not transcribed in the immature leaves of the late flowering mutant comprising ID1. ID1 is a DNA binding protein that expressed in the immature leaves, controlling the production of the "putative" floringen (Colasanit, et al., (1998) *Cell* 93:593-603). The loss of FTM1 and 2 transcription in the ID1 mutant indicated that FTM1 and 2 are downstream from the ID1 gene in the same flowering pathway.

SVP1, 2 and 3 genes show the distinct pattern of expression in the SAM and immature leaves. SVP1 and SVP3 genes are expressed in both tissues during the vegetative stage and decline sharply during and after the floral transition. They show no difference in the mutant backgrounds. This pattern of expression is consistent with their role as the repressors of flowering, working upstream of ID1 and DLF. However the duplicate gene, SVP2 showed a pattern of expression similar to FTM1 and 2, being at the low level during the vegetative stage and increasing sharply during the floral transition. This pattern is more consistent with SVP2s role as an activator of flowering.

Example 15

In Situ Hybridization of FTM1, 2, 3 and SVP1, 2, 3 Genes

In situ localization of FTM 1, 2 and 3 transcripts was performed on the male inflorescence tissues (tassel primordial) at seedling stage V5-6 just after the floral transition. FTM1 and FTM2 transcripts showed signals evenly distributed across the rib zone of the primordial central spike (rachis). No signal was detected in the central zone of the apical meristem or in the lateral branches. Some signal was detected in the surrounding emerging leaves. These data suggest that the FTM1 and 2 function may be associated with switching development programs from leaf formation to initiation of floral formation. The FTM1 and 2 function most likely as flowering-time genes. In situ localization of FTM3 transcripts showed that FTM3 was expressed in the central zone of all tassel meristems, including the main inflorescence meristems, spikelet pair meristems and branch meristems. Strong signals were detected in the vascular stands of the central spike. Weak signals were seen in the immature leaves surrounding young tassels. Because the central zone of the meristems contains pluripotent stem cells, these data suggest that FTM3 plays a role in meristem maintenance.

In situ localization of SVP1, 2, and 3 transcripts was performed on the shoot apical meristem at seedling V3-V4 stages, before the floral transition. SVP1 signals were detected in the peripheral zone of the SAM mostly in the zone of leaf initiation. There was very little signal in the immature leaves. The SVP2 gene has a similar pattern, but overall it is much stronger and more significant in the leaf primordia and immature leaves. Neither SVP1 nor SVP2 were expressed in the central zone of the SAM. These data suggest the genes role in the fate of organ determination. SVP3 transcripts showed a different pattern from SVP1 and 2. SVP3 is expressed in the whole zone of the SAM, including the central, peripheral and rib zones and in leaf primordia and emerging immature leaves. The expression pattern suggests that SVP1 and 2 and SVP3 play a distinct role in the floral transition.

Example 16

Over Expression of FTM2 and SVP1 and 2 in Transgenic Plants

Figure 5:
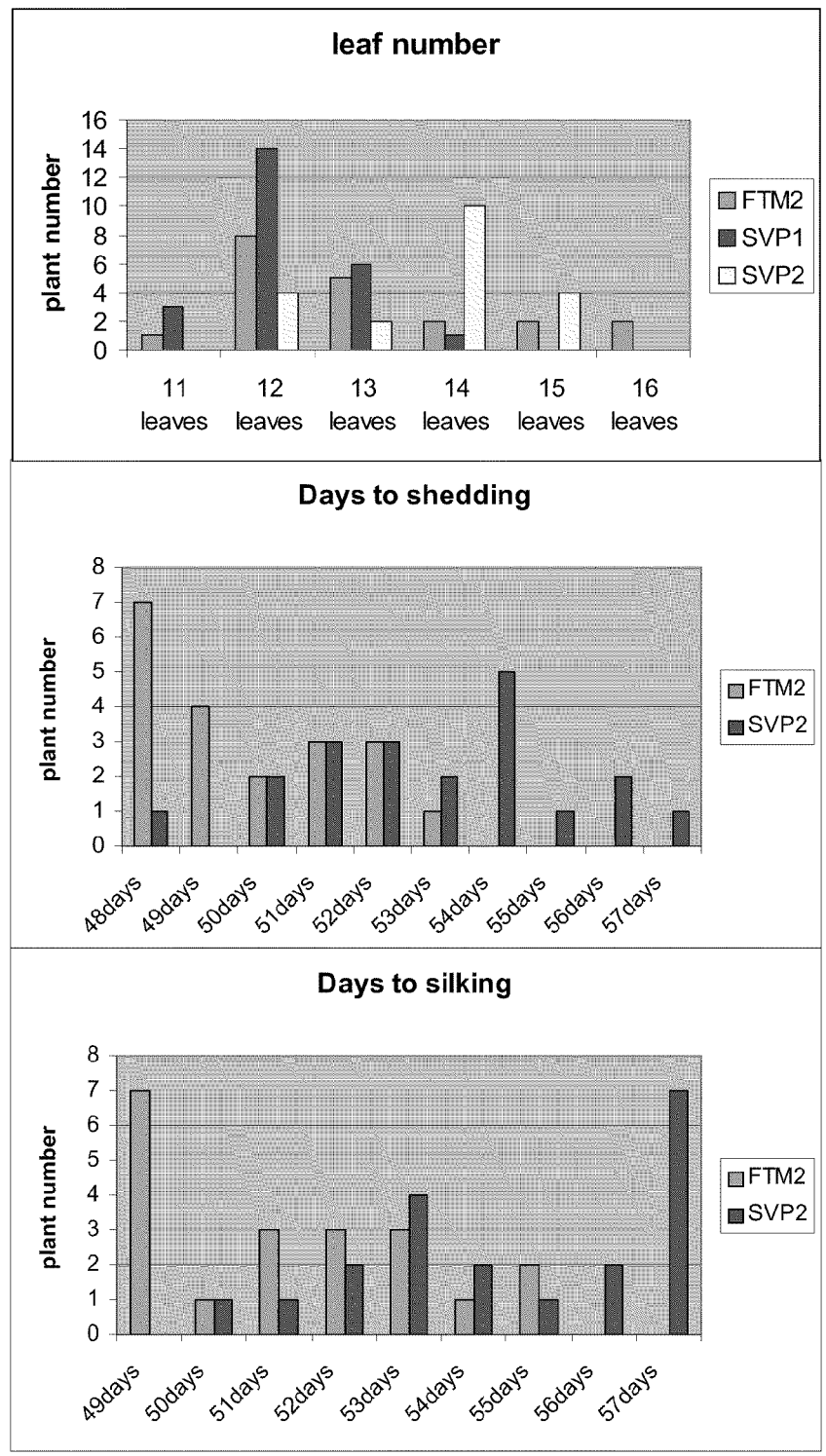
FIG. 5 provides expression of FTM2 and SVP1/2 in transgenic plants. Transgenic plants over-expressing FTM2, SVP1 and SVP2 genes were produced according the standard Pioneer procedure for Agro-bacterium transformation. cDNA were constitutively expressed under the UBIQITIN promoter. The transition from vegetative to reproductive development can be measured by the number of leaves that plant produced at the maturity of the plant. A leaf number analysis indicated FTM2 and SVP1 genes contribute to early flowering. However, FTM2 had stronger effects on flowering than SVP2, because FTM2 transgenics began shedding (pollen production) and silking a week earlier (on average) than SVP2 plants. The FTM2 and SVP1 transgenic plants did not show any phenotypic abnormalities. They produced normal ears and tassels suggesting that ectopic expression of FTM2 and SVP1 MADS box genes did not change meristem identity but changed only the flowering time. Ectopic expression of SVP2 caused abnormalities in ears and tassels, which can be described as changing the organ identity. Some spikelets on the tassels were converted into female gametophytes, producing silking ovules that were fertile and produced kernels after pollination. Multiple ears (up to 4) emerged from the same lateral bud. Glumes surrounding ovules were overgrown and greenish, making ears with vegetative appearance. The SVP2 gene may be characterized functionally as the flower-meristem identity gene.

Transgenic plants over-expressing FTM2, SVP1 and SVP2 genes were produced according to standard procedures for *Agrobacterium* transformation, (see, U.S. Pat. No. 5,591,616.) The associated data is presented in FIG. 5. cDNA were constitutively expressed under the UBIQITIN promoter. The transition from vegetative to reproductive development can be measured by the number of leaves that plant produced at the maturity of the plant. Early flowering plants produce less leaves than later flowering plants (Koorneef, et al., (1998) *A. Rev. Plant. Physiol. Plant Mol. Biol.* 49:345-370). FTM2 and SVP1 transgenic plants produced (on average) 2 leaves less than SVP2 transgenic plants. A leaf number analysis indicated FTM2 and SVP1 genes contribute to early flowering. However, FTM2 had stronger effects on flowering than SVP2, because FTM2 transgenics began shedding (pollen production) and silking a week earlier (on average) than SVP2 plants. The FTM2 and SVP1 transgenic plants did not show any phenotypic abnormalities. They produced normal ears and tassels suggesting that ectopic expression of FTM2 and SVP1 MADS box genes did not change meristem identity but changed only the flowering time. These two genes may be considered as flowering time genes with distinct functions: FTM2 as an activator and SVP1 as a repressor of the floral transition. Ectopic expression of SVP2 caused abnormalities in ears and tassels, which can be described as changing the organ identity. Some spikelets on the tassels were converted into female gametophytes, which produced silking ovules, that were fertile and produced kernels after pollination. Multiple ears (up to 4) emerged from the same lateral bud. Glumes surrounding ovules were overgrown and greenish, making ears with a vegetative appearance. The SVP2 gene may be characterized functionally as the flower-meristem identity gene.

Example 17

Chemically Regulated Floral Transition—a Method to Create Programmable Plants Floral transition is an important agronomic trait affecting the time a plant sheds pollen and silks production, which influences crop yields. The floral transition results from the integration of endogenous and environmental signals. A chemically regulated system that controls the switch from vegetative to reproductive development can optimize flowering time for specific environmental conditions during particular growing seasons. For example, farmers can control the floral transition, thereby determining whether increased grain yields or silage-quality plants are produced, depending upon specific weather conditions of a particular year. Such a system may be designed using the FTM1 and FTM2 genes, which are major activators of flowering in corn, under a chemically inducible expression system. A number of chemically inducible systems are known in plants (reviewed in Inducible Gene Expression in Plants (1999) Reynolds PHS (ed), CAB International Publishing Wallingford, Oxfordshier). Unger, et al., (2002) *Transgenic Research* 11:455-465 describe an inducible expression system (VGEcR) for corn, successfully tested in the green house and in the field with reproducible results. Based on the VGEcR system, an inducible cassette to regulate the floral transition would be composed of the FTM1/FTM2 cDNAs downstream of the GAL4 DNA binding sites and any desirable promoter (e.g., a strong promoter such as the S35 promoter) that drives expression of the chimeric ecdysone receptor fused with the GAL4 DNA biding domain. This chimeric ecdysone receptor will accumulate in the cytoplasm as an inactive molecule until the ligand (methoxyfenozide) is applied. In the presence of the ligand, the ecdysone receptor is activated, transported into the nucleus and drives expression of the target gene(s), which are the FTM1 and 2 cDNAs. Therefore, application of the chemical inducer (methoxyfenozide) causes accumulation of FTM1 and FTM2 proteins that direct the switch from vegetative to reproductive development, inducing flowering. Other chemicals or inducible systems may be used in a similar manner to control FTM1 and FTM2 protein accumulation.

Using a similar inducible system, it will be possible to create vernalized (winter) corn varieties. Like typical winter crops such as winter rye, wheat and barley (reviewed in Andersen, et al., (2004) *Trends in Plant Sci.* 9:105-106), the corn flowering activators genes FTM1 and FMT2 may be placed under control of cold-inducible repressors such as the wheat VRN2 protein (Yan, et. al., (2004) *Science* 303:1640-1644). Stacked with cold-tolerance genes, such transgenic lines may be engineered in such a way as to mimic winter crops. This "winter" corn variety may be used in regions where winter crops are routinely grown.

Example 18

Meristem-Specific Promoters of FTM1, 2, 3 and SVP1, 2, 3 Genes

The FTM1, 2, 3 and SVP1, 2, 3 genes are expressed within different zones of the shoot apical meristem (see, example 15, In situ hybridization). These genes are the source of the meristem-specific promoters. The shoot apical meristem is a growing point of the plant. In corn, cell division in the shoot apical meristem occurs for only the first three to four weeks and stops at about the time that the collar of the fifth leaf becomes visible (V5). All of the leaves, all of the stem nodes and all of the ears are initiated from cells produced during cell division in the apical meristem. Once cell division stops, no additional ears or leaves can be formed. At V5, the apical meristem changes from an area of cell division to an embryonic tassel. Thus, the shoot apical meristem plays a vital role in corn organ generation.

Promoter sequences of the FTM and SVP genes were identified from the BAC genomic sequences as segments located between the translation initiation codon ATG and the intergenic regions marked by the sequence homology (see, example 11, Genomic Sequences). The promoter sequences are identified as follows:

FTM1 promoter—SEQ ID NO: 29
FTM2 promoter—SEQ ID NO: 30
FTM3 promoter—SEQ ID NO: 31
SVP1 promoter—SEQ ID NO: 32
SVP2 promoter—SEQ ID NO: 33
SVP3 promoter—SEQ ID NO: 34

The FTM1,2,3 promoters possess typical TATA-boxes, which are a characteristic feature of many plant genes. FTM1 and FTM2 promoters have an auxin response element TGTCTC (Goda, et al., (2004) *Plant Phys* 1334:1555-1573), suggesting that FTM1 and FTM2 genes may be induced by hormone auxin. FTM1 and FTM3 promoters have A-box (TACGTA), C-box (GACGTC) and G-box (CACGTG) elements which are binding sites for bZIP (basic leucine zipper) transcription factors in plants (*Trends in Plant Sci* (2002) 7:106-111). These features suggest that FTM1 and FTM3 genes are transcribed by bZIP transcription factors, which regulate diverse processes including light and stress signaling, seed maturation and flower development.

The promoters of SVP1 and SVP2 genes are TATA-less and do not have any recognizable motifs. However, there are two TATA-boxes within the SVP3 promoter suggesting a different type of regulation of this gene than SVP1 and SVP2 promoters.

Meristem specific or preferred promoters are extremely useful tools for genetic improvement and manipulations at the dividing and growing areas of the plant. The meristem promoter will allow one to target the expression of desired proteins in the meristem to modulate plant growth. It could also be used to protect these meristem areas from injury by herbicides or insects. This meristem promoter can be used to express regulatory proteins that control cell division and growth or enzymes that modulate plant hormone synthesis or other plant growth regulators. Meristem promoters can be used for protection against insect damage. Most insects like to feed on young growing tissues such as apical meritstems, consequently stunting the plant growth. By using meristem promoters to express insecticidal proteins, the tender and rapidly growing parts of the meristem can be protected from insect damage. Meristem promoters can also be used to prevent damage by herbicides at the growing apical meristem. Rapidly growing apical meristem is extremely sensitive to herbicide damage. Therefore, to protect the mersistem areas from injury by the herbicide and allow continue growth of the plant, a meristem promoter could be used to express additional herbicide deactivation enzyme or the herbicide insensitive catalytic enzyme in these sensitive meristem areas. This would effectively protect the tissues at the growing zones of the plants.

Meristem promoters can be used to modulate flowering time, an important agronomic trait. The over-expression of genes that are activators or repressors of flowering in transgenics under the direction of a meristem specific promoter allows one to control the timing of flower formation without ectopic expression of unwanted proteins in other tissues. Controlling manipulation of flowering time provides opportunities for enhancing crop yield, adaptation of germplasm to different climatic zones and synchronous flowering for hybrid seed production.

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is:

1. An isolated polynucleotide wherein the polynucleotide functions as a promoter, which comprises the nucleotide sequence set forth in SEQ ID NO: 30.

2. A recombinant expression cassette comprising the promoter of claim 1.

3. An isolated host cell comprising the polynucleotide of claim 1.

4. A transgenic plant comprising the polynucleotide of claim 1.

5. The transgenic plant of claim 4, wherein said plant is a monocot.

6. The transgenic plant of claim 4, wherein said plant is a dicot.

7. The transgenic plant of claim 4, wherein said plant is selected from the group consisting of: maize, soybean, sunflower, sorghum, canola, wheat, alfalfa, cotton, rice, barley, millet, peanut and cocoa.

8. A transgenic seed from the transgenic plant of claim 4, wherein the seed comprises said polynucleotide.

9. A method of modulating the flowering time in a plant, comprising:
   a. introducing into a plant cell a recombinant expression cassette comprising the polynucleotide of claim 1 operably linked to a nucleic acid encoding a polypeptide involved in flowering time; and
   b. culturing a plant under plant cell growing conditions; wherein the flowering time in said plant is modulated.

10. The method of claim 9, wherein the plant cell is from a plant selected from the group consisting of: maize, soybean, sunflower, sorghum, canola, wheat, alfalfa, cotton, rice, barley, millet, peanut and cocoa.

11. A method of modulating the flowering time in a plant, comprising:
   a. introducing into a plant cell a recombinant expression cassette comprising the polynucleotide of claim 1 operably linked to a nucleic acid encoding a polypeptide involved in flowering time;
   b. culturing the plant cell under plant cell growing conditions; and
   c. regenerating a plant from said plant cell; wherein the flowering time in said plant is modulated.

12. The method of claim 11, wherein the plant is selected from the group consisting of: maize, soybean, sorghum, canola, wheat, alfalfa, cotton, rice, barley, millet, peanut, and cocoa.

13. The method of claim 11, further comprising crossing said plant with another plant to produce hybrid seed.

* * * * *

SEQUENCE LISTING

```
<160> NUMBER OF SEQ ID NOS: 34

<210> SEQ ID NO 1
<211> LENGTH: 1135
<212> TYPE: DNA
<213> ORGANISM: Zea mays

<400> SEQUENCE: 1
gcacgagccg cctttcctct ctctcgctct cctcctctcc tctcctctcc ttccgcatca      60
cacaccacga ctcccaaccg ccggttggct ttgctgctcc gagctcttcc acacccgccc     120
tctctcttgt gggtcggcgg ccgagtgtct gcgtcgtcca cggagatcag ggatcggcgg     180
cggggtatgg cgagggagcg tcgggagata aagaggatag agagcgcggc ggcgcggcag     240
gtcacgttct ccaagcgccg ccgcggcctc ttcaagaagg ctgaggagct ctccgtgctg     300
tgcgatgccg acgtcgcgct catcgtcttc tcctccacgg gaaagctctc ccagttcgcc     360
agctccagta tgaatgagat cattgacaag tacagcacac attctaaaaa cctggggaaa     420
gcagaacagc cttcacttga cttgaactta gaacatagca aatatgcaaa tttgaatgag     480
caacttgtgg aagcaagcct tcgactcagg cagatgagag gtgaagaact tgagggattg     540
agtgttgaag aactccagca attggagaag aatctggaat ctggtctgca tagggtcctt     600
caaacaaagg atcaacaatt cttggaacag atcagcgacc tcgaacaaaa gagtacacaa     660
ctggcagagg agaacaggca actgaggaat caagtatccc acataccccc agttggcaag     720
caatcagttg ctgatgctga aaatgttatc gctgaagatg ggcaatcctc tgaatcagtc     780
atgactgcgt tgcattctgg gagttcacag gataatgatg atggctgcct tgtgttgcat     840
ggaagtgaaa aaacaagatg gtctgtgttg atctgggtgg agctgcggct tcagcagata     900
ggcacttgtg ttattgtctt atggacgacc cccgactact gcaataatct tgcatcggaa     960
gcgagatcag ttaacctgat ttgtcatcct tgtggcttca tgatgcgatg ttgcgcttgt    1020
accgtttgct aggatgttaa ctggactaga atcgtgtcta cttttgtact ggctcgtgaa    1080
tcctatctac tttgtgctat ccaaagttat gaccaaaaaa aaaaaaaaaa aaaaa         1135

<210> SEQ ID NO 2
<211> LENGTH: 377
<212> TYPE: PRT
<213> ORGANISM: Zea mays

<400> SEQUENCE: 2

Ala Arg Ala Ala Phe Pro Leu Ser Arg Ser Pro Pro Leu Leu Ser Ser
  1               5                  10                  15

Pro Ser Ala Ser His Thr Thr Thr Pro Asn Arg Arg Leu Ala Leu Leu
             20                  25                  30

Leu Arg Ala Leu Pro His Pro Pro Ser Leu Leu Trp Val Gly Gly Arg
         35                  40                  45

Val Ser Ala Ser Ser Thr Glu Ile Arg Asp Arg Arg Gly Met Ala
     50                  55                  60

Arg Glu Arg Arg Glu Ile Lys Arg Ile Glu Ser Ala Ala Ala Arg Gln
 65                  70                  75                  80
```

```
Val Thr Phe Ser Lys Arg Arg Arg Gly Leu Phe Lys Lys Ala Glu Glu
                 85                  90                  95

Leu Ser Val Leu Cys Asp Ala Asp Val Ala Leu Ile Val Phe Ser Ser
            100                 105                 110

Thr Gly Lys Leu Ser Gln Phe Ala Ser Ser Ser Met Asn Glu Ile Ile
        115                 120                 125

Asp Lys Tyr Ser Thr His Ser Lys Asn Leu Gly Lys Ala Glu Gln Pro
    130                 135                 140

Ser Leu Asp Leu Asn Leu Glu His Ser Lys Tyr Ala Asn Leu Asn Glu
145                 150                 155                 160

Gln Leu Val Glu Ala Ser Leu Arg Leu Arg Gln Met Arg Gly Glu Glu
                165                 170                 175

Leu Glu Gly Leu Ser Val Glu Glu Leu Gln Gln Leu Glu Lys Asn Leu
            180                 185                 190

Glu Ser Gly Leu His Arg Val Leu Gln Thr Lys Asp Gln Gln Phe Leu
        195                 200                 205

Glu Gln Ile Ser Asp Leu Glu Gln Lys Ser Thr Gln Leu Ala Glu Glu
    210                 215                 220

Asn Arg Gln Leu Arg Asn Gln Val Ser His Ile Pro Pro Val Gly Lys
225                 230                 235                 240

Gln Ser Val Ala Asp Ala Glu Asn Val Ile Ala Glu Asp Gly Gln Ser
                245                 250                 255

Ser Glu Ser Val Met Thr Ala Leu His Ser Gly Ser Ser Gln Asp Asn
            260                 265                 270

Asp Asp Gly Cys Leu Val Leu His Gly Ser Glu Lys Thr Arg Trp Ser
        275                 280                 285

Val Leu Ile Trp Val Glu Leu Arg Leu Gln Gln Ile Gly Thr Cys Val
    290                 295                 300

Ile Val Leu Trp Thr Thr Pro Asp Tyr Cys Asn Asn Leu Ala Ser Glu
305                 310                 315                 320

Ala Arg Ser Val Asn Leu Ile Cys His Pro Cys Gly Phe Met Met Arg
                325                 330                 335

Cys Cys Ala Cys Thr Val Cys Asp Val Asn Trp Thr Arg Ile Val Ser
            340                 345                 350

Thr Phe Val Leu Ala Arg Glu Ser Tyr Leu Leu Cys Ala Ile Gln Ser
        355                 360                 365

Tyr Asp Gln Lys Lys Lys Lys Lys
    370                 375

<210> SEQ ID NO 3
<211> LENGTH: 1236
<212> TYPE: DNA
<213> ORGANISM: Zea mays

<400> SEQUENCE: 3
ctcctctctc gcatcccacc gcatcacaac cacgacttcc tcccgccgcc ggttggcttc      60
gctgctcgtc cacctccgcc cggcccgtgg gacgagtggg gactggagag gtcgcctct     120 gggcttcgcc tctcggcggc cgagtgtctg cgtcgtccac ggagctgaga gcctgagact     180
gagactgaga gcgaccggcg gcggggatgg cgagggagag gcgggagata aagaggatag     240
agagcgcggc agcgaggcag gtcacgttct ccaagcgccg ccgcggcctc ttcaagaagg     300
cccaggagct ctccgtgctg tgcgatgccg acgtcgcgct catcgtcttc tcctccacgg     360
ggaagctctc ccagttcgcc agctccagta tgaatgagat aattgacaag tacaacacgc     420
attctaaaaa cctggggaaa acagaacagc cttcgctgga cttgaactta gagcatagca     480
```

-continued

```
aatatgcaaa tttgaatgag caacttgcgg aagcaagcct tcgactcagg cagatgagag    540
gtgaagaact tgagggattg aatgttgaag aactccagca gttggagaag aacctggaat    600
ctggtctgca tagggtgctt caaacaaagg atcaacaatt cttggaacag atcaatgacc    660
tcgaacgtaa gagtacgcag ctggcagagg agaaacatgca actgaggaat caagtatccc    720
agataccccc agctggcaag caagcagttg ctgatactga aaatgttatt gctgaagaag    780
ggcaatcctc tgaatcagtg atgactgcgt tgcactctgg gagttcacag gataatgatg    840
atggttcgga tgtatctcta aagttagggc tgccttgcgt tgcatggaag taaacaggaa    900
atgaggctcc ttgtcgattc tgggtgtgga tgtgggtgtg ggtggagctg cggcctcagc    960
ggataggcac ttgtgtatgg ttttatggac gaccggcccc cgactacgta ctgcaataat   1020
cttgcattgg aagcgagatc ggttaacctg atttgtcatc cttgtggctt catgatgcga   1080
tgttccgctt gtaccgtttg ctagcatgtt aactgaattt ttagaatcgc atatacttttt   1140
gttcttatat atcactgtcg tactgctcgt aagatgtatc tactttattc tatccaatgt   1200
tgtaacctat cacctaccaa aaaaaaaaaa aaaaaa                              1236
```

<210> SEQ ID NO 4
<211> LENGTH: 394
<212> TYPE: PRT
<213> ORGANISM: Zea mays

<400> SEQUENCE: 4

```
Leu Leu Ser Arg Ile Pro Pro His His Asn His Asp Phe Leu Pro Pro
 1               5                  10                  15

Pro Val Gly Phe Ala Ala Arg Pro Pro Pro Gly Pro Trp Asp Glu
             20                  25                  30

Trp Gly Leu Glu Arg Val Ala Ser Gly Leu Arg Leu Ser Ala Ala Glu
         35                  40                  45

Cys Leu Arg Arg Pro Arg Ser Glu Pro Glu Thr Glu Thr Glu Ser Asp
     50                  55                  60

Arg Arg Arg Gly Trp Arg Gly Arg Gly Arg Arg Gly Arg Ala Arg
 65                  70                  75                  80

Gln Arg Gly Arg Ser Arg Ser Pro Ser Ala Ala Ala Ser Ser Arg
                 85                  90                  95

Arg Pro Arg Ser Ser Pro Cys Cys Ala Met Pro Thr Ser Arg Ser Ser
            100                 105                 110

Ser Ser Pro Pro Arg Gly Ser Ser Pro Ser Ser Pro Ala Pro Val Met
        115                 120                 125

Arg Leu Thr Ser Thr Thr Arg Ile Leu Lys Thr Trp Gly Lys Gln Asn
    130                 135                 140

Ser Leu Arg Trp Thr Thr Ser Ile Ala Asn Met Gln Ile Met Ser Asn
145                 150                 155                 160

Leu Arg Lys Gln Ala Phe Asp Ser Gly Arg Glu Val Lys Asn Leu Arg
                165                 170                 175

Asp Met Leu Lys Asn Ser Ser Ser Trp Arg Arg Thr Trp Asn Leu Val
            180                 185                 190

Cys Ile Gly Cys Phe Lys Gln Arg Ile Asn Asn Ser Trp Asn Arg Ser
        195                 200                 205

Met Thr Ser Asn Val Arg Val Arg Ser Trp Gln Arg Arg Thr Cys Asn
    210                 215                 220

Gly Ile Lys Tyr Pro Arg Tyr Pro Gln Leu Ala Ser Lys Gln Leu Leu
225                 230                 235                 240
```

```
Ile Leu Lys Met Leu Leu Lys Lys Gly Asn Pro Leu Asn Gln Leu
            245                 250                 255

Arg Cys Thr Leu Gly Val His Arg Ile Met Met Val Arg Met Tyr
            260                 265                 270

Leu Ser Gly Cys Leu Ala Leu His Gly Ser Lys Gln Glu Met Arg Leu
            275                 280                 285

Leu Val Asp Ser Gly Cys Gly Cys Gly Cys Gly Trp Ser Cys Gly Leu
            290                 295                 300

Ser Gly Ala Leu Val Tyr Gly Phe Met Asp Asp Arg Pro Pro Thr Thr
305                 310                 315                 320

Tyr Cys Asn Asn Leu Ala Leu Glu Ala Arg Ser Val Asn Leu Ile Cys
            325                 330                 335

His Pro Cys Gly Phe Met Met Arg Cys Ser Ala Cys Thr Val Cys His
            340                 345                 350

Val Asn Ile Phe Arg Ile Ala Tyr Thr Phe Val Leu Ile Tyr His Cys
            355                 360                 365

Arg Thr Ala Arg Lys Met Tyr Leu Leu Tyr Ser Ile Gln Cys Cys Asn
            370                 375                 380

Leu Ser Pro Thr Lys Lys Lys Lys Lys
385                 390

<210> SEQ ID NO 5
<211> LENGTH: 1406
<212> TYPE: DNA
<213> ORGANISM: Zea mays

<400> SEQUENCE: 5
gcacgaggct tgctggctag ggtaggcttc tgttcatgct gctgctgagc caacgcggcc      60
gtcctcatcc tgttcctgtc atccatccac tctctctcct ctccctccct ccctcctctc     120
ctctcctctc ctctcgtctc tctctctctc tcgtcgctat ggctagttc gcgcgtcttg      180 ttccataaat aggagtagta ggcagttcct cgctggtcct ttgcgcaaaa gagtactctc     240
tccctcctac cacacacagc ctccggactg ctccggacgc gcgcctcaga tctactccaa     300
cacctccgca gcggcggcgc cgcgggtgg aggagcagga gaggcggcgc catggtcggg      360
accgggaaga gggagcggat agcgatacgg aggatcgaca acctggcggc caggcaggtg     420
accttctcca agaggcggcg gggcctgttc aagaaggccg aggagctctc catcctctgc     480
gacgccgagg tcggccttgt cgtcttctcc gccaccggca aactcttcca cttcgccagc     540
tccagcatga agcaggtaat cgatcggtac gactctcatt ccaagactct ccagaggtcc     600
gaaccgcagt cgtctcaact gcagtcacat atggatgacg gcacttgtgc aaggctaaag     660
gaggaacttg ctgaaacaag ccttaagctc aggcagatga ggagagga gctccagagg       720 ctgagcgtcg aacagctgca ggagctcgag aagaccctcg aatccggcct cggctctgta     780
ctcaaaacca agagccaaaa aatccttgac gagatcagcg gtctggaaag aaagagaacg     840
cagctgatcg aggagaactc aaggctgaag gagcaagtga cacggatgtc gaggatggag     900
acgcagcttg gcgccgatcc agagttcgtg tacgaggaag ggcagtcgtc tgaatccgtg     960
acgaacacgt cctatccgcg cccgtccacc gacaccgacg actgctccga cacatcgctc    1020
aggctcgggc taccactctt cagctccaag tgacggagat ttgacatgtc cggtagcgga    1080
gcggtgccga ttgcttgccc ttctccactc tagataggtc tggattgggg gagagcaagc    1140
actgctggat cgggaagacc caagtgacca acgcgtcgca tcagaataag gcattttgag    1200
tgctgtatga tgtgtgtatt ctggctctga aagtgagacc tgcttttgtt ataatacata    1260
```

```
catacaggca gcatggcaat acgtgacggg gtatccgctg cctgcagtcc gtgacctgtc    1320
tgtcgtctct gtttctagta aaaaaaaaaa aaaaaaaaaa aaaaaaaaaa aaaaaaaaaa    1380
aaaaaaaaaa aaaaaaaaaa aaaaaa                                         1406
```

<210> SEQ ID NO 6
<211> LENGTH: 455
<212> TYPE: PRT
<213> ORGANISM: Zea mays

<400> SEQUENCE: 6

```
Ala Arg Gly Leu Leu Ala Arg Val Gly Phe Cys Ser Cys Cys Cys Ala
  1               5                  10                  15

Asn Ala Ala Val Leu Ile Leu Phe Leu Ser Ser Ile His Ser Leu Ser
             20                  25                  30

Ser Pro Ser Leu Pro Pro Leu Leu Ser Ser Pro Leu Val Ser Leu Ser
         35                  40                  45

Leu Ser Ser Leu Leu Ala Ser Ser Arg Val Leu Phe His Lys Glu Ala
 50                  55                  60

Val Pro Arg Trp Ser Phe Ala Gln Lys Ser Thr Leu Ser Leu Leu Pro
 65                  70                  75                  80

His Thr Ala Ser Gly Leu Leu Arg Thr Arg Ala Ser Asp Leu Leu Gln
             85                  90                  95

His Leu Arg Ser Gly Gly Ala Arg Gly Trp Arg Ser Arg Gly Gly
            100                 105                 110

Ala Met Val Gly Thr Gly Lys Arg Glu Arg Ile Ala Ile Arg Arg Ile
            115                 120                 125

Asp Asn Leu Ala Ala Arg Gln Val Thr Phe Ser Lys Arg Arg Gly
130                 135                 140

Leu Phe Lys Lys Ala Glu Glu Leu Ser Ile Leu Cys Asp Ala Glu Val
145                 150                 155                 160

Gly Leu Val Val Phe Ser Ala Thr Gly Lys Leu Phe His Phe Ala Ser
                165                 170                 175

Ser Ser Met Lys Gln Val Ile Asp Arg Tyr Asp Ser His Ser Lys Thr
            180                 185                 190

Leu Gln Arg Ser Glu Pro Gln Ser Gln Leu Gln Ser His Met Asp
        195                 200                 205

Asp Gly Thr Cys Ala Arg Leu Lys Glu Glu Leu Ala Glu Thr Ser Leu
    210                 215                 220

Lys Leu Arg Gln Met Arg Gly Glu Glu Leu Gln Arg Leu Ser Val Glu
225                 230                 235                 240

Gln Leu Gln Glu Leu Glu Lys Thr Leu Glu Ser Gly Leu Gly Ser Val
                245                 250                 255

Leu Lys Thr Lys Ser Gln Lys Ile Leu Asp Glu Ile Ser Gly Leu Glu
            260                 265                 270

Arg Lys Arg Thr Gln Leu Ile Glu Glu Asn Ser Arg Leu Lys Glu Gln
        275                 280                 285

Val Thr Arg Met Ser Arg Met Glu Thr Gln Leu Gly Ala Asp Pro Glu
    290                 295                 300

Phe Val Tyr Glu Glu Gly Gln Ser Ser Glu Ser Val Thr Asn Thr Ser
305                 310                 315                 320

Tyr Pro Arg Pro Ser Thr Asp Thr Asp Cys Ser Asp Thr Ser Leu
                325                 330                 335

Arg Leu Gly Leu Pro Leu Phe Ser Ser Lys Arg Arg Phe Asp Met Ser
            340                 345                 350
```

-continued

Gly Ser Gly Ala Val Pro Ile Ala Cys Pro Ser Pro Leu Ile Gly Leu
      355                 360                 365

Asp Trp Gly Arg Ala Ser Thr Ala Gly Ser Gly Arg Pro Lys Pro Thr
370                 375                 380

Arg Arg Ile Arg Ile Arg His Phe Glu Cys Cys Met Met Cys Val Phe
385                 390                 395                 400

Trp Leu Lys Asp Leu Leu Leu Leu Tyr Ile His Thr Gly Ser Met Ala
              405                 410                 415

Ile Arg Asp Gly Val Ser Ala Ala Cys Ser Pro Pro Val Cys Arg Leu
              420                 425                 430

Cys Phe Lys Lys Lys Lys Lys Lys Lys Lys Lys Lys Lys Lys Lys Lys
              435                 440                 445

Lys Lys Lys Lys Lys Lys Lys
      450                 455

<210> SEQ ID NO 7
<211> LENGTH: 1278
<212> TYPE: DNA
<213> ORGANISM: Zea mays

<400> SEQUENCE: 7 atacccctc cccctccgat ccgtcgcggc agcgctcatc accgctttaa atccgcctcc      60
tcccagcgtc tccctcctcc cggcctgtcc cctcacctcc ctcccctat ctctccaccg     120
ccgcagctag ctgcgacgtc atgcactcgc cggcgccacc gccaccgcat actatctaca     180
attagccagc cgtaggctta cctatcctgt gtcaagcaag cctctcgcaa gcaacaagga     240
aggaagctag ctagttttat agctgctgtc ggcggcggcg gctgaagcga cgtgcctgag     300
ctaggattta ggttgagatc aggagaggga gaaggcggcg gcgatggggc gcgggaaggt     360
gcagctgaag cggatcgaga caagatcaa ccgccaggtg acattctcca gcgccgctc      420
ggggctactc aagaaggcgc acgagatctc cgtgctctgc gacgccgagg tcgcgctcat     480
catcttctcc accaagggca agctctacga gtactctacc gattcatgta tggacaaaat     540
tcttgaacgg tatgagcgct actcctatgc agaaaaggtt ctcatttccg cagaatatga     600
aactcagggc aattggtgcc atgaatatag aaaactaaag gcgaaggtcg agacaataca     660
gaaatgtcaa aagcacctca tgggagagga tcttgaaact ttgaatctca aagagcttca     720
gcaactagag cagcagctgg agagttcact gaaacatatc agaacaagga agagccagct     780
tatggtcgag tcaatttcag cgctccaacg gaaggagaag tcactgcagg aggagaacaa     840
ggttctgcag aaggagctcg cggagaagca gaaagaccag cggcagcaag tgcaacggga     900
ccaaactcaa cagcagacca gttcgtcttc cacgtccttc atgttaaggg aagctgcccc     960
aacaacaaat gtcagcatct tccctgtggc agcaggcggg agggtggtgg aaggggcagc    1020
agcgcagccg caggctcgcg ttggactgcc accatggatg cttagccatc tgagctgctg    1080
aaggtttgcc ctcaccgtcg cgatgtgata gcccaaaatc cagcaagtct tccccggacc    1140
ccggactgtc cccgcttctc cgcctggtgc agtatcgtcg tgatcgcgag aagcagcagc    1200
agcggtttgc cgtatttttt accactgtgt ataagtagca tatctgcaat gtgtatattt    1260
tgttcaccgt tcctgctg                                                  1278

<210> SEQ ID NO 8
<211> LENGTH: 417
<212> TYPE: PRT
<213> ORGANISM: Zea mays

-continued

<400> SEQUENCE: 8

```
Ile Pro Pro Pro Pro Ile Arg Arg Gly Ser Ala His His Arg Phe
 1               5                  10                  15

Lys Ser Ala Ser Ser Gln Arg Leu Pro Pro Gly Leu Ser Pro His
             20                  25                  30

Leu Pro Pro Ile Ser Pro Pro Gln Leu Ala Ala Thr Ser Cys
             35                  40                  45

Thr Arg Arg Arg His Arg His Arg Ile Leu Ser Thr Ile Ser Gln Pro
 50                  55                  60

Ala Tyr Leu Ser Cys Val Lys Gln Ala Ser Lys Gln Gln Gly Arg
 65                  70                  75                  80

Lys Leu Ala Ser Phe Ile Ala Ala Val Gly Gly Gly Ser Asp Val
                 85                  90                  95

Pro Glu Leu Gly Phe Arg Leu Arg Ser Gly Glu Gly Glu Gly Gly
                100                 105                 110

Asp Gly Ala Arg Glu Gly Ala Ala Glu Ala Asp Arg Glu Gln Asp Gln
                115                 120                 125

Pro Pro Gly Asp Ile Leu Gln Ala Pro Leu Gly Ala Thr Gln Glu Gly
130                 135                 140

Ala Arg Asp Leu Arg Ala Leu Arg Arg Gly Arg Ala His His Leu
145                 150                 155                 160

Leu His Gln Gly Gln Ala Leu Arg Val Leu Tyr Arg Phe Met Tyr Gly
                165                 170                 175

Gln Asn Ser Thr Val Ala Leu Leu Cys Arg Lys Gly Ser His Phe
                180                 185                 190

Arg Arg Ile Asn Ser Gly Gln Leu Val Pro Ile Lys Thr Lys Gly Glu
                195                 200                 205

Gly Arg Asp Asn Thr Glu Met Ser Lys Ala Pro His Gly Arg Gly Ser
210                 215                 220

Asn Phe Glu Ser Gln Arg Ala Ser Ala Thr Arg Ala Ala Ala Gly Glu
225                 230                 235                 240

Phe Thr Glu Thr Tyr Gln Asn Lys Glu Glu Pro Ala Tyr Gly Arg Val
                245                 250                 255

Asn Phe Ser Ala Pro Thr Glu Gly Glu Val Thr Ala Gly Gly Glu Gln
                260                 265                 270

Gly Ser Ala Glu Gly Ala Arg Gly Glu Ala Glu Arg Pro Ala Ala Ala
                275                 280                 285

Ser Ala Thr Gly Pro Asn Ser Thr Ala Asp Gln Phe Val Phe His Val
290                 295                 300

Leu His Val Lys Gly Ser Cys Pro Asn Asn Lys Cys Gln His Leu Pro
305                 310                 315                 320

Cys Gly Ser Arg Arg Glu Gly Gly Gly Arg Gly Ser Ser Ala Ala Ala
                325                 330                 335

Gly Ser Arg Trp Thr Ala Thr Met Asp Ala Pro Ser Glu Leu Leu Lys
                340                 345                 350

Val Cys Pro His Arg Arg Asp Val Ile Ala Gln Asn Pro Ala Ser Leu
                355                 360                 365

Pro Arg Thr Pro Asp Cys Pro Arg Phe Ser Ala Trp Cys Ser Ile Val
                370                 375                 380

Val Ile Ala Arg Ser Ser Ser Ser Gly Leu Pro Tyr Phe Leu Pro Leu
385                 390                 395                 400
```

Cys Ile Ser Ser Ile Ser Ala Met Cys Ile Phe Cys Ser Pro Phe Leu
            405                 410                 415

Leu

<210> SEQ ID NO 9
<211> LENGTH: 1369
<212> TYPE: DNA
<213> ORGANISM: Zea mays

<400> SEQUENCE: 9

```
atcaagtcgg ggcaacgcgc atcactcgct ttaaatccgc acctcccggc cggtcccctt    60
atcacctcac cttctccttt gagtcctctc tctccgccgc cgcagctagc tgtgacgtta   120
tgctctcgcc ggcgccatag cgccagcgcc taccgtctac aactatccag ccttaggctt   180
acctatcccg tcaatcaagc ctctcgtaag gaacaaggaa ggtagctagc tagttctata   240
gctgctgtcg tcgtcgtcat cggcggcggc ggcgcctgtt cttagaggat aaggttgtcc   300
tagcggagag ggagctagcc aggatttcgg ttgagatcaa gaggggagc aggcggcggc   360
ggcggcgatg gggcgcggga aggtgcagct gaagcggatc gagaacaaga tcaaccgcca   420
ggtgaccttc tccaagcgcc gctcgggcgt gcccaagaag gcgcacgaga tctccgtgct   480
ctgcgacgcc gaggtcgcgc tcatcatctt ctccaccaaa gggaagctct acgagtattc   540
caccgattca tgtatggaca aaattcttga ccggtacgag cgctactcct atgcagaaaa   600
ggttcttatt tcagcagaat ctgaaactca gggcaattgg tgccacgagt atagaaaact   660
aaaggcgaag gtcgagacaa tacaaaaatg tcaaaagcac ctcatgggag aggatcttga   720
aacgttgaat ctcaaagagc ttcagcaact agagcagcag ctggagagtt cactgaaaca   780
tatcagaacc aggaagaacc aactatgct cgagtcaatt tcggagctcc aacgaagga   840
gaagtcgctg caggaggaga acaaggttct gcagaaggag ctcgcggaga agcagaaagc   900
ccagcggaag caagtgcaat gggggccaaac ccaacagcag accagttcgt cttcctcgtg   960
cttcgtgata agggaagctg ccccaacaac aaatatcagc attttcctg tggcagcagg  1020
cgggaggttg gtggaaggtg cagcagcgca gccacaggct cgcgttggac taccaccatg  1080
gatgcttagc cacctgagca gctgaaggtt tcagcaactc ttccgttta tccgcctggt  1140
gcagtatagt atcatcgtga tcgcgagagc agcagcagtg ggttgcccgt atcttttttt  1200
accaatgtat gtctatatat gtaagtatca aatctgcaat gtgttaatca ccatttccgc  1260
tggggcggcc gcacgagtac tttacgcatc agtatatgtg cagcatcaaa tattccatt   1320
tcatgaccat aagacgttct tgatcaaaaa aaaaaaaaaa aaaaaaaaa             1369
```

<210> SEQ ID NO 10
<211> LENGTH: 443
<212> TYPE: PRT
<213> ORGANISM: zea mays

<400> SEQUENCE: 10

Ile Lys Ser Gly Gln Arg Ala Ser Leu Ala Leu Asn Pro His Leu Pro
 1               5                  10                  15

Ala Gly Pro Leu Ile Thr Ser Pro Ser Pro Leu Ser Pro Leu Ser Pro
            20                  25                  30

Pro Pro Gln Leu Ala Val Thr Leu Cys Ser Arg Arg Arg His Ser Ala
        35                  40                  45

Ser Ala Tyr Arg Leu Gln Leu Ser Ser Leu Arg Leu Thr Tyr Pro Val
    50                  55                  60

```
Asn Gln Ala Ser Arg Lys Glu Gln Gly Arg Leu Ala Ser Ser Ile Ala
 65                  70                  75                  80

Ala Val Val Val Ile Gly Gly Gly Ala Cys Ser Arg Ile Arg
             85                  90                  95

Leu Ser Arg Arg Gly Ser Pro Gly Phe Arg Leu Arg Ser Arg Gly Gly
             100                 105                 110

Ala Gly Gly Gly Gly Asp Gly Ala Arg Glu Gly Ala Ala Glu Ala
             115                 120                 125

Asp Arg Glu Gln Asp Gln Pro Pro Gly Asp Leu Leu Gln Ala Pro Leu
             130                 135                 140

Gly Ala Ala Gln Glu Gly Ala Arg Asp Leu Arg Ala Leu Arg Arg Arg
145                 150                 155                 160

Gly Arg Ala His His Leu Leu His Gln Arg Glu Ala Leu Arg Val Phe
                165                 170                 175

His Arg Phe Met Tyr Gly Gln Asn Ser Pro Val Arg Ala Leu Leu Leu
             180                 185                 190

Cys Arg Lys Gly Ser Tyr Phe Ser Arg Ile Asn Ser Gly Gln Leu Val
             195                 200                 205

Pro Arg Val Lys Thr Lys Gly Glu Gly Arg Asp Asn Thr Lys Met Ser
210                 215                 220

Lys Ala Pro His Gly Arg Gly Ser Asn Val Glu Ser Gln Arg Ala Ser
225                 230                 235                 240

Ala Thr Arg Ala Ala Ala Gly Glu Phe Thr Glu Thr Tyr Gln Asn Gln
                245                 250                 255

Glu Glu Pro Thr Tyr Ala Arg Val Asn Phe Gly Ala Pro Thr Glu Gly
             260                 265                 270

Glu Val Ala Ala Gly Gly Glu Gly Ser Ala Glu Gly Ala Arg Gly
             275                 280                 285

Glu Ala Glu Ser Pro Ala Glu Ala Ser Ala Met Gly Pro Asn Pro Thr
290                 295                 300

Ala Asp Gln Phe Val Phe Leu Val Leu Arg Asp Lys Gly Ser Cys Pro
305                 310                 315                 320

Asn Asn Lys Tyr Gln His Phe Ser Cys Gly Ser Arg Arg Glu Val Gly
             325                 330                 335

Gly Arg Cys Ser Ser Ala Ala Thr Gly Ser Arg Trp Thr Thr Thr Met
             340                 345                 350

Asp Ala Pro Pro Glu Gln Leu Lys Val Ser Ala Thr Leu Pro Val Tyr
             355                 360                 365

Pro Pro Gly Ala Val Tyr His Arg Asp Arg Glu Ser Ser Ser Gly
             370                 375                 380

Phe Ala Val Ser Phe Phe Thr Asn Val Cys Leu Tyr Met Val Ser Asn
385                 390                 395                 400

Leu Gln Cys Val Asn His His Phe Arg Trp Gly Gly Arg Thr Ser Thr
                405                 410                 415

Leu Arg Ile Ser Ile Cys Ala Ala Ser Asn Ile Pro Phe Ser Pro Asp
             420                 425                 430

Val Leu Asp Gln Lys Lys Lys Lys Lys Lys
             435                 440

<210> SEQ ID NO 11
<211> LENGTH: 1304
<212> TYPE: DNA
<213> ORGANISM: zea mays
```

<400> SEQUENCE: 11

```
ctctctccgc cgccgcagct agctgtgacg ttatgctctc gccggcgcca tagcgccagc      60
gcctaccgtc tacaactatc cagccttagg cttacctatc ccgtcaatca agcctctcgt     120
aaggaacaag gaaggtagct agctagttct atagctgctg tcgtcgtcgt catcggcggc     180
ggcggcgcct gttcttagag gataaggttg tcctagcgga gagggagcta gccaggattt     240
cggttgagat caagagggg agcaggcggc ggcggcggcg atggggcgcg ggaaggtgca      300
gctgaagcgg atcgagaaca agatcaaccg ccaggtgacc ttctccaagc gccgctcggg     360
gctgctcaag aaggcgcacg agatctccgt gctctgcgac gccgaggtcg cgctcatcat     420
cttctccacc aaagggaagc tctacgagta ttccaccgat tcatgtatgg acaaaattct     480
tgaccggtac gagcgctact cctatgcaga aaaggttctt atttcagcag aatctgaaac     540
tcagggcaat tggtgccacg agtatagaaa actaaaggcg aaggtcgaga caatacaaaa     600
atgtcaaaag cacctcatgg gagaggatct tgaaacgttg aatctcaaag agcttcagca     660
actagagcag cagctggaga gttcactgaa acatatcaga accaggaaga accaacttat     720
gctcgagtca atttcggagc tccaacggaa ggagaagtcg ctgcaggagg agaacaaggt     780
tctgcagaag gagaaagcgt tgctcctgcc tgcagctcgc ggagaagcag aaagcccagc     840
ggaagcaagt gcaatggggc caacccaac agcagaccag ttcgtcttcc tcgtgcttcg     900
tgataaggga agctgccca caacaaata tcagcatttt tcctgtggca gcaggcggga     960
ggttggtgga aggtgcagca gcgcagccac aggctcgcgt tggactacca ccatggatgc    1020
ttagccacct gagcagctga aggtttcagc aactcttccc gtttatccgc ctggtgcagt    1080
atagtatcat cgtgatcgcg agagcagcag cagtgggttt gccgtatctt tttttaccaa    1140
tgtatgtcta tatatgtaag tatcaaatct gcaatgtgtt aatcaccatt tccgctgggg    1200
cggccgcacg agtactttac gcatcagtat atgtgcagca tcaaatattc cattttcatg    1260
accataagac gttcttgatc aaaaaaaaaa aaaaaaaaaa aaaa                      1304
```

<210> SEQ ID NO 12
<211> LENGTH: 420
<212> TYPE: PRT
<213> ORGANISM: zea mays

<400> SEQUENCE: 12

```
Leu Ser Pro Pro Gln Leu Ala Val Thr Leu Cys Ser Arg Arg Arg
  1               5                  10                  15

His Ser Ala Ser Ala Tyr Arg Leu Gln Leu Ser Ser Leu Arg Leu Thr
             20                  25                  30

Tyr Pro Val Asn Gln Ala Ser Arg Lys Glu Gln Gly Arg Leu Ala Ser
         35                  40                  45

Ser Ile Ala Ala Val Val Val Ile Gly Gly Gly Ala Cys Ser
     50                  55                  60

Arg Ile Arg Leu Ser Arg Arg Gly Ser Pro Gly Phe Arg Leu Arg Ser
 65                  70                  75                  80

Arg Gly Gly Ala Gly Gly Gly Gly Asp Gly Ala Arg Glu Gly Ala
                 85                  90                  95

Ala Glu Ala Asp Arg Glu Gln Asp Gln Pro Gly Asp Leu Leu Gln
            100                 105                 110

Ala Pro Leu Gly Ala Ala Gln Glu Gly Ala Arg Asp Leu Arg Ala Leu
        115                 120                 125

Arg Arg Arg Gly Arg Ala His His Leu Leu His Gln Arg Glu Ala Leu
    130                 135                 140
```

```
Arg Val Phe His Arg Phe Met Tyr Gly Gln Asn Ser Pro Val Arg Ala
145                 150                 155                 160

Leu Leu Leu Cys Arg Lys Gly Ser Tyr Phe Ser Arg Ile Asn Ser Gly
            165                 170                 175

Gln Leu Val Pro Arg Val Lys Thr Lys Gly Glu Gly Arg Asp Asn Thr
        180                 185                 190

Lys Met Ser Lys Ala Pro His Gly Arg Gly Ser Asn Val Glu Ser Gln
            195                 200                 205

Arg Ala Ser Ala Thr Arg Ala Ala Gly Glu Phe Thr Glu Thr Tyr
        210                 215                 220

Gln Asn Gln Glu Glu Pro Thr Tyr Ala Arg Val Asn Phe Gly Ala Pro
225                 230                 235                 240

Thr Glu Gly Glu Val Ala Ala Gly Gly Glu Gln Gly Ser Ala Glu Gly
                245                 250                 255

Glu Ser Val Ala Pro Ala Cys Ser Ser Arg Ser Arg Lys Pro Ser
            260                 265                 270

Gly Ser Lys Cys Asn Gly Ala Lys Pro Asn Ser Arg Pro Val Arg Leu
        275                 280                 285

Pro Arg Ala Ser Gly Lys Leu Pro Gln Gln Ile Ser Ala Phe Phe
290                 295                 300

Leu Trp Gln Gln Ala Gly Gly Trp Trp Lys Val Gln Arg Ser His
305                 310                 315                 320

Arg Leu Ala Leu Asp Tyr His His Gly Cys Leu Ala Thr Ala Glu
            325                 330                 335

Gly Phe Ser Asn Ser Ser Arg Leu Ser Ala Trp Cys Ser Ile Val Ser
        340                 345                 350

Ser Ser Arg Glu Gln Gln Gln Trp Val Cys Arg Ile Phe Phe Tyr Gln
    355                 360                 365

Cys Met Ser Ile Tyr Val Ser Ile Lys Ser Ala Met Cys Ser Pro Phe
370                 375                 380

Pro Leu Gly Arg Pro His Glu Tyr Phe Thr His Gln Tyr Met Cys Ser
385                 390                 395                 400

Ile Lys Tyr Ser Ile Phe Met Thr Ile Arg Arg Ser Ser Lys Lys Lys
            405                 410                 415

Lys Lys Lys Lys
        420

<210> SEQ ID NO 13
<211> LENGTH: 1288
<212> TYPE: DNA
<213> ORGANISM: zea mays

<400> SEQUENCE: 13
cacgagatgc caagggcccc tccctctccc tcgtcgtcgg gccaattgag tgtgagagct      60
cgaaaaaacc caggggatcg gccggaccag cagcgagcga gcgcgagctc tgcgtgcgtg     120
tgtgtgtctg cgcgctagat tagatcacct ccatcgtcaa taattgcagg cagatccata     180
tagtctgctg gtggcgagac aaagcaacgg atcgtcgtcg atccggagag cggaaagcgc     240
gcagatcgcg gcggccatgg ggcgcgggaa ggtggtgctg cagcggatcg agaacaagat     300
cagccgccag gtcaccttcg ccaagcgccg gaacggcctg ctcaagaagc gtacgagctc     360
tccatcctct gcgacgccga ggtcgcgctc gtcctcttct cgcacgccgg ccgcctctac     420
cagttctcat cctcctccga tctgcttaag actctagagc ggtaccagag gcacatctat     480
gcttcagctg atgctgcagt gccatctagc gatgagatgc agaataacta tcaagaatat     540
```

```
gtgaagctga aagcacgagt tgaggtttta caacactcgc aaaggaatct tcttggtgaa    600
gaactggctc cacttagccc aagtgaactt gaccagcttg agagtcaagt agacaagacc    660
ttgaagcaaa taagatcaag aaagactcag gtgttacttg atgaactttg cgacttaaag    720
agaaaggaac aaatgctgca agacgctaac agggttctga aaaggaagct gcacgagttt    780
gaggcagagg ctgcttctcc cccacaattg gcgtggcaag gcggaggcgg catgttgtcc    840
catgaccctc cacagccaga acacttcttc gtggctctgg agagcaacgc gcctctgcaa    900
cctacatacc atactatgga catgaaccag cagccagagc cagcgccggg cggctgctac    960
cctcctgcgt ggatggctta gccagcgctt tggttccatt gccttgacaa gtgccgtgtc   1020
cttcagagat cgctacgagt cctgctgctg cttttgcgaa ccccccctt gctgcctgcc    1080 atgcttaccg aactgttcaa ataagaaata accacatggt cctatatagg ttgctgttgt   1140
ctttatcttc tgttgatcac gtcctgctca gatgctttaa acgctatgca aaatggctta   1200
gcgatgcacg ctggaatggg ctgaactgct tgtgctttgg gagtataaat cgctcgggcg   1260
cttggcaata aaaaaaaaaa aaaaagaa                                      1288
```

<210> SEQ ID NO 14
<211> LENGTH: 423
<212> TYPE: PRT
<213> ORGANISM: zea mays

<400> SEQUENCE: 14

```
His Glu Met Pro Lys Gly Pro Pro Ser Pro Ser Ser Gly Gln Leu
  1               5                  10                  15

Ser Val Arg Ala Arg Lys Asn Pro Gly Asp Arg Pro Asp Gln Gln Arg
         20                  25                  30

Ala Ser Ala Ser Ser Ala Cys Val Cys Val Ser Ala Arg Ile Arg Ser
     35                  40                  45

Pro Pro Ser Ser Ile Ile Ala Gly Arg Ser Ile Ser Ala Gly Gly Glu
 50                  55                  60

Thr Lys Gln Arg Ile Val Val Asp Pro Glu Ser Gly Lys Arg Ala Asp
 65                  70                  75                  80

Arg Gly Gly His Gly Ala Arg Glu Gly Gly Ala Ala Asp Arg Glu
                 85                  90                  95

Gln Asp Gln Pro Pro Gly His Leu Arg Gln Ala Pro Glu Arg Pro Ala
            100                 105                 110

Gln Glu Ala Tyr Glu Leu Ser Ile Leu Cys Asp Ala Glu Val Ala Leu
        115                 120                 125

Val Leu Phe Ser His Ala Gly Arg Leu Tyr Gln Phe Ser Ser Ser Ser
    130                 135                 140

Asp Leu Leu Lys Thr Leu Glu Arg Tyr Gln Arg His Ile Tyr Ala Ser
145                 150                 155                 160

Ala Asp Ala Ala Val Pro Ser Ser Asp Glu Met Gln Asn Asn Tyr Gln
                165                 170                 175

Glu Tyr Val Lys Leu Lys Ala Arg Val Glu Val Leu Gln His Ser Gln
            180                 185                 190

Arg Asn Leu Leu Gly Glu Glu Leu Ala Pro Leu Ser Pro Ser Glu Leu
        195                 200                 205

Asp Gln Leu Glu Ser Gln Val Asp Lys Thr Leu Lys Gln Ile Arg Ser
    210                 215                 220

Arg Lys Thr Gln Val Leu Leu Asp Glu Leu Cys Asp Leu Lys Arg Lys
225                 230                 235                 240
```

```
Glu Gln Met Leu Gln Asp Ala Asn Arg Val Leu Lys Arg Lys Leu His
                245                 250                 255
Glu Phe Glu Ala Glu Ala Ala Ser Pro Pro Gln Leu Ala Trp Gln Gly
            260                 265                 270
Gly Gly Gly Met Leu Ser His Asp Pro Pro Gln Pro Glu His Phe Phe
        275                 280                 285
Val Ala Leu Glu Ser Asn Ala Pro Leu Gln Pro Thr Tyr His Thr Met
    290                 295                 300
Asp Met Asn Gln Gln Pro Glu Pro Ala Pro Gly Gly Cys Tyr Pro Pro
305                 310                 315                 320
Ala Trp Met Ala Pro Ala Leu Trp Phe His Cys Leu Asp Lys Cys Arg
                325                 330                 335
Val Leu Gln Arg Ser Leu Arg Val Leu Leu Leu Leu Arg Thr Pro
            340                 345                 350
Pro Leu Leu Pro Ala Met Leu Thr Glu Leu Phe Lys Glu Ile Thr Thr
        355                 360                 365
Trp Ser Tyr Ile Gly Cys Cys Cys Leu Tyr Leu Leu Leu Ile Thr Ser
    370                 375                 380
Cys Ser Asp Ala Leu Asn Ala Met Gln Asn Gly Leu Ala Met His Ala
385                 390                 395                 400
Gly Met Gly Thr Ala Cys Ala Leu Gly Val Ile Ala Arg Ala Leu Gly
                405                 410                 415
Asn Lys Lys Lys Lys Lys Arg
            420

<210> SEQ ID NO 15
<211> LENGTH: 36
<212> TYPE: DNA
<213> ORGANISM: Artificial Sequence
<220> FEATURE:
<223> OTHER INFORMATION: oligonucleotide

<400> SEQUENCE: 15
tcgacccacg cgtccgaaaa aaaaaaaaaa aaaaaa                          36

<210> SEQ ID NO 16
<211> LENGTH: 17
<212> TYPE: DNA
<213> ORGANISM: zea mays

<400> SEQUENCE: 16
gatcggttaa cctgatt                                                17

<210> SEQ ID NO 17
<211> LENGTH: 17
<212> TYPE: DNA
<213> ORGANISM: zea mays

<400> SEQUENCE: 17
gatcagttaa cctgatt                                                17

<210> SEQ ID NO 18
<211> LENGTH: 17
<212> TYPE: DNA
<213> ORGANISM: zea mays

<400> SEQUENCE: 18
gatcgggaag acccaag                                                17
```

-continued

<210> SEQ ID NO 19
<211> LENGTH: 17
<212> TYPE: DNA
<213> ORGANISM: zea mays

<400> SEQUENCE: 19
gatcgcgaga agcagca                                                  17

<210> SEQ ID NO 20
<211> LENGTH: 17
<212> TYPE: DNA
<213> ORGANISM: zea mays

<400> SEQUENCE: 20
gatcgcgaga gcagcag                                                  17

<210> SEQ ID NO 21
<211> LENGTH: 17
<212> TYPE: DNA
<213> ORGANISM: zea mays

<400> SEQUENCE: 21
gatcgctacg agtcctg                                                  17

<210> SEQ ID NO 22
<211> LENGTH: 32
<212> TYPE: DNA
<213> ORGANISM: Artificial Sequence
<220> FEATURE:
<223> OTHER INFORMATION: Primer

<400> SEQUENCE: 22
agagaagcca acgccawcgc ctcyatttcg tc                                 32

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
ggtttcgacc gtacgaggaa agacc                                         25

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
tataccatgt ggtgcggcca caggt                                         25

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25
ttcgcgggga tcatgtgggt aatcg                                         25

```
<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
agtaggcagt tcctcactgg tcctttgcg                                      29

<210> SEQ ID NO 27
<211> LENGTH: 28
<212> TYPE: DNA
<213> ORGANISM: Artificial Sequence
<220> FEATURE:
<223> OTHER INFORMATION: TUSC Primer Ftm3

<400> SEQUENCE: 27
actcttcacc ggtccagcta gtaaatgc                                       28

<210> SEQ ID NO 28
<211> LENGTH: 28
<212> TYPE: DNA
<213> ORGANISM: Artificial Sequence
<220> FEATURE:
<223> OTHER INFORMATION: TUSC Primer Ftm2

<400> SEQUENCE: 28
catacatgta tcgacctcct gctcgctt                                       28

<210> SEQ ID NO 29
<211> LENGTH: 1649
<212> TYPE: DNA
<213> ORGANISM: Zea mays
<220> FEATURE:
<221> NAME/KEY: misc_feature
<222> LOCATION: 58, 139, 220, 301, 382, 463, 544, 625, 706, 787, 868,
      949, 1030, 1111, 1192, 1273, 1354, 1435, 1516, 1597
<223> OTHER INFORMATION: n = A,T,C or G

<400> SEQUENCE: 29
gatagcactg ttgctgtaga cctgtagccg ccgcatcgtg ctcgtgcagc agcagcangg     60
actgcaggag acacaggtgt cccgcattgg cccgtcccg tcgtggcctg ccgctgccg     120 tcggaccggc ccaaaagtng ggcggcccct tgctgcgtca gcccgcccca cgcgttgtcc   180
gcctctccgg actgcgaaaa gtgaccgagc cgggaaaccn aggcgaccag ttgctgcccc   240
ttccccgttt tgcccaaaca ttaccccgca gacttcatca cgtgcacggc gtacggtgcg   300
ncttaaaaaa gcaaaataaa aataaaaacc ccgacgagcc gcatactcca aacaatctga   360
tatctttaat gcttgggcac cngctgcacg tggcaccagc acggccgtgc aaattaattt   420
gaaagcaaaa cattccgata caaaaaatga caacaacgaa tcntagttag atctatttaa   480
aacaatacct ccattctcga atatttatcg tccactagtt cagttttaa cgcgcgcgac   540 aaantaaaaa agaactaaga aagtatacta ctccactacc atcctaatgc ctactttgag   600
taatctagta ttgatcctaa tccantatgt attaaggtgg tttgcagtat aacttaaact   660
aatttacata taatccacct caacacatat ggattatggt caatanctag agtatccaaa   720
caaagcttaa ggattgtttg gtttctaact atttttttaat ccatccattt tatttttattt  780 tagaccncta aactaataaa tacgataact aaaatagaac ccaaacaccc atagagacta   840
aacaccccct aaaacaagtc ttgttctnca tatgttagag tcaaacgttt ttattttaa     900 taaaacatat aaaaataaca ctaatagttt taatatataa atagaattna atagatggag   960
```

-continued

```
cgttggtttt tttgtgtaat aaatttattc gaagatacta ctgctaatac tttggtcgaa    1020
aataaatgtn tatagcgata ttcattatag ctaccagtag tcgagtggag tagatagaaa    1080
caaaaacaga taatagctgc tgcctgccag ncatcttgtc gtcattactt catgccaggc    1140
aaggtgtgtg agagaagccg gtttcgaccg tacgaggaaa gaccctggca gncgggccct    1200
tgcgatgaga gatgccgtgg ggccaggtgg gcccgggcac gccgcatcgg ccaatgccag    1260
ttcgacagcg gcnggcgggg aaaccatccc ggtttcgcta taccccctcc ccctccgatc    1320
cgtcgcggca gcgctcatca ccgctttaaa tccngcctcc tcccagcgtc tccctcctcc    1380
cggcctgtcc cctcacctcc ctcccccata ctctccaccg ccgcagctag ctgcngacgt    1440
catgcactcg ccggcgccac cgccaccgca tactatctac aattagccag ccgtaggctt    1500
acctatcctg tgtcanagca agcctctcgc aagcaacaag gaaggaagct agctagtttt    1560
atagctgctg tcggcggcgg cggctgaagc gacgtgncct gagctaggat ttaggttgag    1620
atcaggagag ggagaaggcg gcggcgatg                                      1649
```

<210> SEQ ID NO 30
<211> LENGTH: 2457
<212> TYPE: DNA
<213> ORGANISM: Zea mays

<400> SEQUENCE: 30

```
tcagtgtttt ttttaaaaaa atacactact ttactccagg aatgactagg acaacataga      60
tagatagtga aggaaaaaat agtggcggcc cttgccaaca tcttttggtc atgagagcaa     120
gtataataag gtgatgtaga tggactgcat gcgatgccac gccagatttt aaaaatgtgg     180
aacaaagaga agtggagaaa aaactgggt tgctccctag tagccagctg agagtgggtt      240
ggacacggac tctaaagact cactgttaga gagaggttga ccgaatatta aatatacaac     300
cggtatcctc gaagaattat tatataaatg attgtctata tgtgacatga caacataaca     360
aaccaactat agactacata ttactctctc tgtactaaaa tataattcat tttacgctaa     420
ttacacattc attaattaac ttatgaatgt agtttgtatg tatatctaca ttcattatct     480
tctattcaaa tgtagataga aaagagtat tagaactata ttttttgggac agaaggagta    540 tcaattagag ggtgtttggt ttatagggac ttagtccctc aatttttattc ttattcagtc    600 cataaattga caaatacaaa aactgaaatt aagttttaga ttctatattt gacaatttag     660
atactataat aaaattgaga gattaaaaag taatccctag aaatcaaata tatactatac     720
ttaaagcacc agtttcaacg gtcgtcatgc gtcattttt tacaaataac ccctcacagc      780
tatttcaaat taatccgctg cacgtttata gatgtcaaac gacgcccgac acgggctaga    840
tgcacgcggg ccacaactat ggcacaggca cgtcatgccg gcctgctaac tgtgtcgggc     900
cagctcgtta gcttatcgat ccatttaatt aaatcagcgt aacgacgccc gacacgggct    960
aaatgcacgc gggccacaac tatggcacaa acacgtcatg ccggcctact aactgtgtcg    1020
ggccagcccg ttatcccgtc gatccattta attaaatcag cgtaaaatgt ttaaaaatgg    1080
tgcaggaggt ggggttcgaa cccatgcctt ggtggaagga gggcgggaga cactgggtga    1140
aactgtctaa tcaatagaac atcacgctaa gatgttttta atattgaata taaattgtat    1200
ataggtatat acatttttt tgtaaaataa aaaataatc gtgtctggcc gggcgagcac     1260
tacgagccga ggctacaacc caagtacgac acgacattct tggctcttgc aagtattagg    1320
tcgtttctga gaccacattg gcgcaatgaa ctacatggtg tttaagattg ctgtattgga    1380
tggagtagca atgatttgtc acactaacat caaaatgaaa ggttatttgt tggttttaaa    1440
```

```
cattagtatt tgctatgaag tagcataatt tatatagagc gcatccagtt tttattgatg    1500
cctgacttta gcaattactc catattttga tctatctttt ttataagttt gacttcatag    1560
gacttatttt agaaacttga tctcataaac tttctcttat ttggtctatg tatgatggaa    1620
ttatgtcatt ttataatctc tgttcattca gtcaatcgtt gtgaactctc ttctaatcgc    1680
tcacttcatt gaccgtgtta taccaagaca tatttgtatg gagtaaacaa ttatatcagt    1740
tagctaaatc aaaaaatata ttatacaaag agtggagaca atcaataaaa aatcttgatt    1800
tttttatgaa taatttatgt gggcattatt gtaaaccgtg gcaactcaca ttcaatacac    1860
ttcgtgcgag aggctagctg cgactagctg cgagattgga atggatccgg tttcgaccgt    1920
acgaggaagg acgctggccc aggcagtggg tccttgggat gggagatgcg gtggggcccg    1980
acgggcccgg ccgcggggca tcggctaatg ggagttcgac aacggcagcc tcggaaccca    2040
tcccggtttc gcgataccCC ctccctgctc cctcctcccc tcccctccga tcaagtcggg    2100
gcaacgcgca tcactcgctt taaatccgca cctcccggcg tctccctcct cccggccggt    2160
ccccttatca cctcaccttc tcctctgagt cctctctctc cgccgccgca gctagctgtg    2220
acgttatgct ctcgccggcg ccatagcgcc agcgcctacc gtctacaact atccagcctt    2280
aggcttacct atcccgtcaa tcaagcctct cgtaaggaac aaggaaggta gctagctagt    2340
tcgtcatcgg cggcggcggc gcctgttctt agaggataag gttgtcgtag cggagaggga    2400
gctagccagg attttggttg agatcaggag ggggagcagg cggcggcggc ggcgatg    2457

<210> SEQ ID NO 31
<211> LENGTH: 2128
<212> TYPE: DNA
<213> ORGANISM: Zea mays

<400> SEQUENCE: 31
tagtttgata actctatttt tataaagcat tctcattttt aaaagagaaa atgaactaat      60
ttatttttag aaaataaaaa tctttcaaaa aatggtgttg tcaaaactaa tccttatgcg     120
acaatttaaa cttttcgggg aggagcagaa cactggattt aactagagta gagcatgtat     180
gactccatta attatgttga gtgggctcta aaaggatacg ttaaaaaaga atcaatagac     240
gttggtgtgg ggggaggcta cgtacggccc caagctgtca tcattgacga tcctactact     300
ggggtggcca ggcgtggcct actcctgtag aggagttgcg ctcactgtgt cctcccctcc     360
tccaccctga gtccctgaca cggcgggagg ccgcgtggga cgtcggtcac gtgagagggt     420
cagaggggac gacgagtcga cgacccgccg ggccgataca tggcccctcg acgcgacgtg     480
catgcactac tgtgctcgct ctacgtatgc ttcgttccaa cttccaccag ccgcgtccaa     540
tcccgccaca agtgccgcga cgagccacac ccacacgtac ggtcgtacac tacgtacggc     600
gcgcgcgcac gtgtgtcaga ttgactggct cggccgggtg cgacgcaacc cgaggcggaa     660
ggaaccaccg aacgccgcgc tgcctcgccc atgccgaccg cccggtcggg ggacgccgtg     720
acgggtaaac agagcttccg agcttgcact agcttgcgct gcttggtttg gttccgttcc     780
ttctcgcgac tgtgccgccg gcatgctggg ccgccgagtt gcgggagcgc aggggctctc     840
tgctgtggtg gtgtggctta atttcgggca tttcgcgcgg caccaacgcg ggctcgacac     900
gtcctcatta aattcgggcc ctgtgcgtgc ctgtgcgcgc gcagcagcga gcgacccgga     960
tatctgcctc ggattcgccg cctcgcctct ctctctctcc ggccgatccc caattgtgcc    1020
cgtccctcgc gccgctgccg agcttttggg ctactgctac tgggctcgcc gcgctcatca    1080
gggcaaacgc atactacgct acaagtgaag tgagtgatcg atgacgacgg tagctagcta    1140
```

-continued

| | |
|---|---|
| gctagctagt tggtgcggt tctcgtcgga ctatgggctg tttggttctg ctttttttctg | 1200 |
| accagctttt cttagaatct ggctgtggaa agaatctggc tgtgtagaga atctgagtat | 1260 |
| cattatgatt acgtgcggag gaagataaag gtgtccatag gactgaggat ctagaaagtg | 1320 |
| acggatttct actattgcaa caactcaacc gattatgtgt ttatgttgat gttgaatggt | 1380 |
| ttttaaccaa acgaatttta tagaagctga ctgaaaagct aagcgtttgg cagtccgcag | 1440 |
| cagttttttgg tggccagaag ctccaaaaag ctgaaacaaa cagggcttta tttggtgctt | 1500 |
| caccgccgga gccaggctag ctatacactt tgtagttgtt tgtaggggta tataggagca | 1560 |
| gtatctacag tagcagcact cttcaccggt ccagctagta aatgcggtat ctgtcgtctg | 1620 |
| tcgagctaac ctatcatatc agcgccatgc gccccggccg gtcgtaacct agctaggagt | 1680 |
| agctagctag gactagctag ctaggagcct aagcgcccag cccagtgggt ggtagcctac | 1740 |
| caagggtgag gaagaggagc tgagctagga ccgcgaggcg agcgagatcc aatctgcacc | 1800 |
| ccacgaacga aaagattctt ccccgccggc gtcgctctct catccgtcga cgtctcgctc | 1860 |
| cttccttcct ctctctctct ctctctctct ctctctctct ttctctctct cagccagcag | 1920 |
| caagcatata gcccagcacc accacatgcc caagggccct ccctctccct cgtcgtcggg | 1980 |
| ccaattgagt gtgagagctc gaaaaaaccc aggggatcgg ccggaccagc agcgagcgag | 2040 |
| cgcgagctct gcgtgcgtgt gtgtgtctgc tctagattag atcacctcca tcgtcaataa | 2100 |
| ttgcaggcag atccatagtc tgctggtg | 2128 |

<210> SEQ ID NO 32
<211> LENGTH: 1029
<212> TYPE: DNA
<213> ORGANISM: Zea mays

<400> SEQUENCE: 32

| | |
|---|---|
| gcccaggact gactgatacg cccccagaat caaacggagc aaaagcagac tgtgtccata | 60 |
| attacccaga ccaagctgat ggaaccggcg ggagtaatga atacaacaac ctggcgcgaa | 120 |
| gcagcacgca ccgtgttcac tgatgaagcg aagcgagggc agatcgatct gcgcgagatc | 180 |
| cgggcggccc gccaaatccc cgggggccgg ggcggcgcgc ggcacagcgg tgcaccacag | 240 |
| aatcggggcc ggaacagcga atccgggcgg atgcagcaca gcagcagtac gcgctacgcg | 300 |
| gccaacccaa tccaatcgaa gcgaaggcgc agcacagcat cttctcttcc ttcccacccc | 360 |
| cgccggcttt ctccctgatt tgtgattttc ccacaacgcc gcagagtgag gctgaggcta | 420 |
| cggcagggca gccagccagc agagagcgca ccgtcaccgc gcaccacgcg gccgcctgct | 480 |
| acaggctgta ctgttctggt ccggcagcac ccacccggcc acccctcact cggtcactcc | 540 |
| gcagtccgca ctctcccttt ccttttcagg aatcatctac ctcgcccgct ggcaccatc | 600 |
| cctacgctac gcctcgtcta ctgcctgctg tcatgctgtg cgtgggtggg cgggccccgc | 660 |
| cgcgccgttc cgtgtggcga ggggagcata acaatgact gactgggccg gccggccggc | 720 |
| cccgtagcca ttcgtctgcc tttccctctc ccagtttccg ttttttttaat gctttgttta | 780 |
| ctcgcgggga tcatgggta atcgcgtggg ccgtgcctgg ctgggtttat ttatgccgac | 840 |
| ctgccaattg gagcaaatcc cctttcctgc ccctccccct ccgcctttcc tctctctcgc | 900 |
| tctcctcctc tcctctccctc tcctctcctt ccgcatcaca caccacgact cccaaccgcc | 960 |
| ggttggcttt gctgctccga gctcttcctc ttccacaccc gccctctctc ttgggtcggc | 1020 |
| ggccgagtg | 1029 |

```
<210> SEQ ID NO 33
<211> LENGTH: 1287
<212> TYPE: DNA
<213> ORGANISM: Zea mays

<400> SEQUENCE: 33
aaaaaaatgt gcacataccc tatcggctaa ccacttattg tttcgactta tcgatgcaca      60
cacaccagac accaccaaac catatctcac gttgatgtga ctttgctttt catacacgat     120
tggtgtggtt gtttggtact gacactacgt ggaatcagaa cgaaacttgt caagaactga     180
ccgatacgct catacgcccc cagaatcaaa cggaacaagc aaaccatccg tgtccatgat     240
tacccagacc aaaagctgag cgaaaccccg gaggcgggcg gggggagggt aataatcaat     300
gcaacaacct gccgacgagt gttcactgat gacgcatgcc gagaggaaat ctgcgcgaga     360
tccggccggg gcggcggggc gctggcgcgc tgcggcgcgg cgtggcgctg cacagcggtg     420
ccggtgcgcc acagaatcgg gccggaacag cgaatccggg cggctacagc agtacgcggc     480 caccccaat caccaatcga aggtcacccc caatctgcgg ccgcgcgcag gcgcagcagc      540
agcatcttct ttctcttcct tcacacctcc accaccgccg gctttctcct tgatttccca     600
cgtcgcgcag gagcctgagg ctgaaaccac ggcaggccag ccagctagta gcagagagag     660
agcaccgtca ccgcgcagcg agcacacgcg gccgcctgct acaggctgta ctgtactgtt     720
ctggaccggc aactcacccg gccacccctc actccctttc cttttcagga acaccgcctg     780
cttggcacca tccctacgcg ggctacgccg ccctcgtcta ctgcctgcgc ctggctgggc     840
cccgccgcgg ccgttccgtg tgacgagggg agcataaaca atgactgggc cggccggccc     900
cgtagccatt ccccaactt ccgcttccgc tctcacagtt tttatgcttt gtttattcgc      960
ggggatcatg tgggtaatcg cgtgggtcgt gcgcccgtgc ctggctgggt ttatttacgc    1020
cgacctgcca ataggagcaa atccctggcc cctctccttg gcttttcctc tcgctctcct    1080
cctctctcgc atcccaccgc atcacaacca cgacttcctc ccgccgccgg ttggcttcgc    1140
tgctcgtcca cctccgcccg gcccgtggga cgagtgggga ctggagaggg tcgcctctgg    1200
gcttcgcctc tcggcggccg agtgtctgcg tcgtccacgg agctgagagc ctgagactga    1260
gactgagagc gaccggcggc ggggatg                                       1287

<210> SEQ ID NO 34
<211> LENGTH: 925
<212> TYPE: DNA
<213> ORGANISM: Zea mays

<400> SEQUENCE: 34
cacaggcagc acaaccccgt ttagcccatc ggaccatccg cggtgccttg gttcttcctc      60
tctaccgaga aaaacacccc aaaacagtat cttcagaagg gagtaaaaaa agggtggcta     120
taccaacgct ccaactccaa gagaccagac cgcagaggcg acgcacagta gagtggagcg     180
ccagcaggca gcagcagcgg gtagcagggg cgaggtgacg cgcggaccaa tggcgcggag     240
ggtagggggg cactcgcccc tgaccgcctc gtggccgaca cctggctcca tcggtctggg     300
ggatcggagc agcagcctag caggcaccac ggcgacccct taccataaaa agctactgct     360
ccttcgtacg acgccgtgct gcaagctgcc ctacagctgc agtgcttgct ggctagggta     420
ggcttctgtt catgctgctg ctgagccaac gcggccgtcc tcatcctgtt cctgtcatcc     480
atccactctc tctcctctcc ctccctccct cctctcctct cctctcctct cgtctctctc     540
tctctctcgt cgctattggc tagttcgcgc gtccttgttcc ataaatagga gtagtaggca     600
gttcctcgct ggtcctttgc gcaaaagagt actctctccc tcctaccaca cacagcctcc     660
```

```
ggactgctcc ggacgcgcgc ctcagatcta ctccaacacc tgtaaggatt cctctggccg    720 tgtggcctttt ccggcaacta tagctagggt tctccttctc ccctccctcc gcccgcttgc   780
tcttggacgg tgcttcctct tctttaccag ctagtcaaag taaccacgcg tgctgcttca    840
tctctccctt ccttcctgcc gtgtggttgt tggcagccgc agcggcggcg cccgcgggtg    900
gaggagcagg agaggcggcg ccatg                                          925
```